United States Patent
Kopel et al.

(10) Patent No.: US 12,324,635 B2
(45) Date of Patent: Jun. 10, 2025

(54) SYSTEMS AND METHODS FOR PROVIDING SURGICAL GUIDANCE

(71) Applicant: Covidien LP, Mansfield, MA (US)

(72) Inventors: Evgeni Kopel, Barkan (IL); Oren P. Weingarten, Hod-Hasharon (IL); Ariel Birenbaum, Raanana (IL)

(73) Assignee: Coviden LP, Mansfield, MA (US)

( * ) Notice: Subject to any disclaimer, the term of this patent is extended or adjusted under 35 U.S.C. 154(b) by 0 days.

(21) Appl. No.: 18/608,799

(22) Filed: Mar. 18, 2024

(65) Prior Publication Data

US 2024/0216078 A1     Jul. 4, 2024

Related U.S. Application Data

(63) Continuation of application No. 16/936,354, filed on Jul. 22, 2020, now Pat. No. 11,931,111.

(Continued)

(51) Int. Cl.
*A61B 8/00* (2006.01)
*A61B 1/267* (2006.01)
(Continued)

(52) U.S. Cl.
CPC ............ *A61B 34/20* (2016.02); *A61B 1/2676* (2013.01); *A61B 34/10* (2016.02); *A61B 34/25* (2016.02);
(Continued)

(58) Field of Classification Search
CPC .................................................... A61B 34/20
See application file for complete search history.

(56) References Cited

U.S. PATENT DOCUMENTS 6,373,916 B1   4/2002   Inoue et al.
6,473,634 B1   10/2002   Barni
(Continued)

FOREIGN PATENT DOCUMENTS

BR     0013237 A    7/2003
BR     0116004 A    6/2004
(Continued)

OTHER PUBLICATIONS

Extended European Search Report issued in European Application No. 20195111.8 dated Feb. 5, 2021; 8 pages.

*Primary Examiner* — Joel F Brutus
(74) *Attorney, Agent, or Firm* — Weber Rosselli & Cannon LLP

(57) ABSTRACT

Surgical guidance systems and methods visually mark a structure of interest (SOI) of an organ on intraoperative images captured by a locatable imaging device. A location of the SOI relative to a body structure (e.g., a passageway system) associated with the organ is determined in a preoperative image that is captured by a medical diagnostic imaging (MDI) system. The location of the SOI relative to the body structure in the preoperative image is then mapped onto a reconstructed version of the body structure based on location information provided by localization sensors distributed on the body structure. An intraoperative image taken by the locatable imaging device is aligned with the reconstructed version of the body structure and an image object representing the SOI is overlaid on the intraoperative image at a location that is mapped from the reconstructed version of the body structure.

20 Claims, 9 Drawing Sheets

Related U.S. Application Data

(60) Provisional application No. 62/897,436, filed on Sep. 9, 2019.

(51) Int. Cl.
  *A61B 34/00* (2016.01)
  *A61B 34/10* (2016.01)
  *A61B 34/20* (2016.01)
  *A61B 90/00* (2016.01)
  *G06T 7/00* (2017.01)

(52) U.S. Cl.
  CPC ........ *A61B 90/37* (2016.02); *A61B 2034/105* (2016.02); *A61B 2034/107* (2016.02); *A61B 2034/2055* (2016.02); *A61B 2034/2065* (2016.02); *A61B 2090/365* (2016.02); *G06T 7/0014* (2013.01); *G06T 2207/10016* (2013.01); *G06T 2207/10081* (2013.01); *G06T 2207/20221* (2013.01); *G06T 2207/30061* (2013.01)

(56) References Cited

U.S. PATENT DOCUMENTS

| | | | |
|---|---|---|---|
| 7,551,759 B2 | 6/2009 | Hristov et al. | |
| 7,916,918 B2 | 3/2011 | Suri et al. | |
| 8,335,359 B2 | 12/2012 | Fidrich et al. | |
| 8,482,606 B2 | 7/2013 | Razzaque et al. | |
| 8,625,869 B2 | 1/2014 | Harder et al. | |
| 8,706,184 B2 | 4/2014 | Mohr et al. | |
| 8,827,934 B2 | 9/2014 | Chopra et al. | |
| 9,433,390 B2 | 9/2016 | Nathaniel et al. | |
| 9,833,167 B2 | 12/2017 | Cohen et al. | |
| 9,888,898 B2 | 2/2018 | Imagawa et al. | |
| 9,918,659 B2 | 3/2018 | Chopra et al. | |
| 10,127,629 B2 | 11/2018 | Razzaque et al. | |
| 10,130,316 B2 | 11/2018 | Funabasama et al. | |
| 10,373,719 B2 | 8/2019 | Soper et al. | |
| 10,376,178 B2 | 8/2019 | Chopra | |
| 10,405,753 B2 | 9/2019 | Sorger | |
| 10,478,162 B2 | 11/2019 | Barbagli et al. | |
| 10,480,926 B2 | 11/2019 | Froggatt et al. | |
| 10,524,866 B2 | 1/2020 | Srinivasan et al. | |
| 10,555,788 B2 | 2/2020 | Panescu et al. | |
| 10,610,306 B2 | 4/2020 | Chopra | |
| 10,638,953 B2 | 5/2020 | Duindam et al. | |
| 10,674,970 B2 | 6/2020 | Averbuch et al. | |
| 10,682,070 B2 | 6/2020 | Duindam | |
| 10,706,543 B2 | 7/2020 | Donhowe et al. | |
| 10,709,506 B2 | 7/2020 | Coste-Maniere et al. | |
| 10,772,485 B2 | 9/2020 | Schlesinger et al. | |
| 10,796,432 B2 | 10/2020 | Mintz et al. | |
| 10,823,627 B2 | 11/2020 | Sanborn et al. | |
| 10,827,913 B2 | 11/2020 | Ummalaneni et al. | |
| 10,835,153 B2 | 11/2020 | Rafii-Tari et al. | |
| 10,885,630 B2 | 1/2021 | Li et al. | |
| 10,896,506 B2 | 1/2021 | Zhao et al. | |
| 2003/0013972 A1 | 1/2003 | Makin | |
| 2005/0182295 A1 | 8/2005 | Soper et al. | |
| 2012/0289825 A1 | 11/2012 | Rai et al. | |
| 2013/0303945 A1 | 11/2013 | Blumenkranz et al. | |
| 2014/0035798 A1 | 2/2014 | Kawada et al. | |
| 2015/0148690 A1 | 5/2015 | Chopra et al. | |
| 2015/0265368 A1 | 9/2015 | Chopra et al. | |
| 2016/0157939 A1 | 6/2016 | Larkin et al. | |
| 2016/0183841 A1 | 6/2016 | Duindam et al. | |
| 2016/0192860 A1 | 7/2016 | Allenby et al. | |
| 2016/0287344 A1 | 10/2016 | Donhowe et al. | |
| 2016/0302747 A1 | 10/2016 | Averbuch | |
| 2017/0007350 A1* | 1/2017 | Popovic | A61B 1/00165 |
| 2017/0112576 A1 | 4/2017 | Coste-Maniere et al. | |
| 2017/0209071 A1 | 7/2017 | Zhao et al. | |
| 2017/0265952 A1 | 9/2017 | Donhowe et al. | |
| 2017/0311844 A1 | 11/2017 | Zhao et al. | |
| 2017/0319165 A1 | 11/2017 | Averbuch | |
| 2018/0078318 A1 | 3/2018 | Barbagli et al. | |
| 2018/0153621 A1 | 6/2018 | Duindam et al. | |
| 2018/0235709 A1 | 8/2018 | Donhowe et al. | |
| 2018/0240237 A1 | 8/2018 | Donhowe et al. | |
| 2018/0256262 A1 | 9/2018 | Duindam et al. | |
| 2018/0263706 A1 | 9/2018 | Averbuch | |
| 2018/0279852 A1 | 10/2018 | Rafii-Tari et al. | |
| 2018/0325419 A1 | 11/2018 | Zhao et al. | |
| 2018/0368917 A1 | 12/2018 | Dekel et al. | |
| 2019/0000559 A1 | 1/2019 | Berman et al. | |
| 2019/0000560 A1 | 1/2019 | Berman et al. | |
| 2019/0008413 A1 | 1/2019 | Duindam et al. | |
| 2019/0038365 A1 | 2/2019 | Soper et al. | |
| 2019/0065209 A1 | 2/2019 | Mishra et al. | |
| 2019/0110839 A1 | 4/2019 | Rafii-Tari et al. | |
| 2019/0110843 A1* | 4/2019 | Ummalaneni | A61B 1/000094 |
| 2019/0175062 A1 | 6/2019 | Rafii-Tari et al. | |
| 2019/0183318 A1 | 6/2019 | Froggatt et al. | |
| 2019/0183585 A1 | 6/2019 | Rafii-Tari et al. | |
| 2019/0183587 A1 | 6/2019 | Rafii-Tari et al. | |
| 2019/0192234 A1 | 6/2019 | Gadda et al. | |
| 2019/0209016 A1 | 7/2019 | Herzlinger et al. | |
| 2019/0209043 A1 | 7/2019 | Zhao et al. | |
| 2019/0216548 A1 | 7/2019 | Ummalaneni | |
| 2019/0239723 A1 | 8/2019 | Duindam et al. | |
| 2019/0239831 A1 | 8/2019 | Chopra | |
| 2019/0246946 A1 | 8/2019 | Kopel et al. | |
| 2019/0250050 A1 | 8/2019 | Sanborn et al. | |
| 2019/0254649 A1 | 8/2019 | Walters et al. | |
| 2019/0269470 A1 | 9/2019 | Barbagli et al. | |
| 2019/0272634 A1 | 9/2019 | Li et al. | |
| 2019/0298160 A1 | 10/2019 | Ummalaneni et al. | |
| 2019/0298451 A1 | 10/2019 | Wong et al. | |
| 2019/0320878 A1 | 10/2019 | Duindam et al. | |
| 2019/0320937 A1 | 10/2019 | Duindam et al. | |
| 2019/0336238 A1 | 11/2019 | Yu et al. | |
| 2019/0343424 A1 | 11/2019 | Blumenkranz et al. | |
| 2019/0350659 A1 | 11/2019 | Wang et al. | |
| 2019/0365199 A1 | 12/2019 | Zhao et al. | |
| 2019/0365479 A1 | 12/2019 | Rafii-Tari | |
| 2019/0365486 A1 | 12/2019 | Srinivasan et al. | |
| 2019/0380787 A1 | 12/2019 | Ye et al. | |
| 2020/0000319 A1 | 1/2020 | Saadat et al. | |
| 2020/0000526 A1 | 1/2020 | Zhao | |
| 2020/0008655 A1 | 1/2020 | Schlesinger et al. | |
| 2020/0030044 A1 | 1/2020 | Wang et al. | |
| 2020/0030461 A1 | 1/2020 | Sorger | |
| 2020/0038750 A1 | 2/2020 | Kojima | |
| 2020/0043207 A1 | 2/2020 | Lo et al. | |
| 2020/0046431 A1 | 2/2020 | Soper et al. | |
| 2020/0046436 A1 | 2/2020 | Tzeisler et al. | |
| 2020/0054399 A1 | 2/2020 | Duindam et al. | |
| 2020/0060771 A1 | 2/2020 | Lo et al. | |
| 2020/0069192 A1 | 3/2020 | Sanborn et al. | |
| 2020/0077870 A1 | 3/2020 | Dicarlo et al. | |
| 2020/0078095 A1 | 3/2020 | Chopra et al. | |
| 2020/0078103 A1 | 3/2020 | Duindam et al. | |
| 2020/0085514 A1 | 3/2020 | Blumenkranz | |
| 2020/0109124 A1 | 4/2020 | Pomper et al. | |
| 2020/0129045 A1 | 4/2020 | Prisco | |
| 2020/0129239 A1 | 4/2020 | Bianchi et al. | |
| 2020/0138515 A1 | 5/2020 | Wong | |
| 2020/0155116 A1 | 5/2020 | Donhowe et al. | |
| 2020/0170623 A1 | 6/2020 | Averbuch | |
| 2020/0170720 A1 | 6/2020 | Ummalaneni | |
| 2020/0179058 A1 | 6/2020 | Barbagli et al. | |
| 2020/0188038 A1 | 6/2020 | Donhowe et al. | |
| 2020/0205903 A1 | 7/2020 | Srinivasan et al. | |
| 2020/0205904 A1 | 7/2020 | Chopra | |
| 2020/0214664 A1 | 7/2020 | Zhao et al. | |
| 2020/0229679 A1 | 7/2020 | Zhao et al. | |
| 2020/0242767 A1 | 7/2020 | Zhao et al. | |
| 2020/0275860 A1 | 9/2020 | Duindam | |
| 2020/0297442 A1 | 9/2020 | Adebar et al. | |
| 2020/0315554 A1 | 10/2020 | Averbuch et al. | |
| 2020/0330795 A1 | 10/2020 | Sawant et al. | |

(56) References Cited

U.S. PATENT DOCUMENTS

2020/0352427 A1  11/2020  Deyanov
2020/0364865 A1  11/2020  Donhowe et al.

FOREIGN PATENT DOCUMENTS

| | | | |
|---|---|---|---|
| CZ | 486540 | B1 | 9/2016 |
| CZ | 2709512 | B6 | 8/2017 |
| CZ | 2884879 | B1 | 1/2020 |
| EP | 3413830 | A4 | 9/2019 |
| EP | 3478161 | A4 | 2/2020 |
| EP | 3641686 | A2 | 4/2020 |
| EP | 3644885 | A1 | 5/2020 |
| EP | 3644886 | A1 | 5/2020 |
| MX | PA03005028 | A | 1/2004 |
| MX | 225663 | B | 1/2005 |
| MX | 226292 | B | 2/2005 |
| MX | 246862 | B | 6/2007 |
| MX | 265247 | B | 3/2009 |
| MX | 284569 | B | 3/2011 |

\* cited by examiner

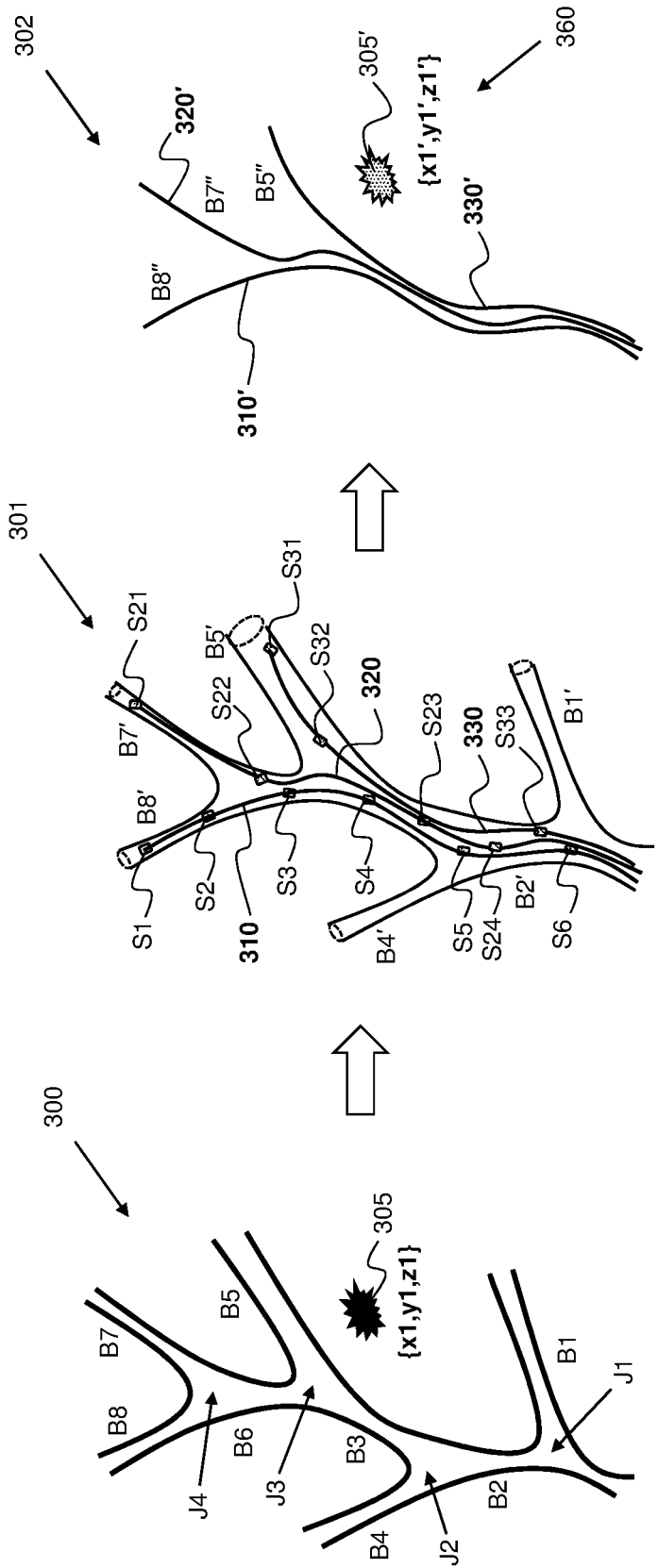

SYSTEMS AND METHODS FOR PROVIDING SURGICAL GUIDANCE

CROSS-REFERENCE TO RELATED APPLICATIONS

This application is a continuation of U.S. application Ser. No. 16/936,354, filed Jul. 22, 2020, now allowed, which claims the benefit of and priority to U.S. Provisional Patent Application No. 62/897,436, filed on Sep. 9, 2019, the contents of each of which are incorporated herein by reference.

FIELD

This disclosure relates to intraoperative guidance during a medical procedure. More particularly, the disclosure is directed to systems and methods for guiding a surgeon to one or more structures of interest (SOIs) within a patient's body, which are invisible to the surgeon, for example, one or more diseased organ portions (DOPs), that reside inside one or more organs (and, therefore, is/are invisible to a surgeon) during a surgical procedure.

BACKGROUND

Endoscopes enable practitioners to examine passageways (e.g., blood vessels, gastrointestinal tract, stomach, airways, etc.) in patient's organs for abnormalities such as foreign bodies, bleeding tumors, inflammation, etc. Bronchoscopy is an example of an endoscopic technique, which involves visualizing the inside of the airways for diagnostic and therapeutic purposes. In a bronchoscopy, a bronchoscope is inserted into the airways, usually through the nose or mouth, or occasionally through a tracheostomy tube. This allows a practitioner to navigate to various areas of the lung so that the practitioner can examine the patient's airways for abnormalities such as foreign bodies, bleeding, tumors, or inflammation.

In some cases, there is a need to reach a location within a patient's body, for example, to resect or remove a diseased portion of an organ (e.g., a lobe of the left or right lung), or a neoplasm that can be benign or cancerous. Removing a neoplasm from, for example, a lung is typically done through the rib cage by using a laparoscope. Surgical instruments used in laparoscopic surgery include: forceps, scissors, probes, dissectors, hooks, retractors, etc. In some cases, blood vessels that are connected to a lobe of the lung must be removed not because the blood vessels are diseased or the lobe is diseased, but because the lobe contains a diseased portion and the entire lobe needs to be resected for oncological reasons.

Surgery may be performed with the aid of one or more imaging devices that utilize one or more imaging techniques such as optical imaging (e.g., via a video camera), thermal imaging, fluoroscopic imaging, and ultrasound imaging. However, each imaging technique has its limitations for each specific SOI. This disclosure is directed to addressing these limitations.

SUMMARY

In one aspect, a method for guiding a surgeon may include identifying (for example, by a controller), in a preoperative image of an organ and a body structure associated with the organ, the body structure and a structure of interest (SOI) in the organ; determining a location of the SOI relative to the body structure in the preoperative image; generating a reconstructed body structure; determining (for example, by the controller) a location of the SOI relative to the reconstructed body structure based on the location of the SOI relative to the body structure in the preoperative image; capturing, by an imaging device, an intraoperative image; determining (for example, by the controller) a location of the imaging device relative to a location of the reconstructed body structure; determining (for example, by the controller) a location of the SOI relative to the intraoperative image based on the location of the SOI relative to the reconstructed body structure and the determined location of the imaging device relative to the location of the reconstructed body structure; producing (for example, by the controller) an image object that represents the SOI; and displaying the intraoperative image with the image object overlaid on the intraoperative image at the location of the SOI relative to the intraoperative image.

In some aspects, the body structure is a passageway system including passageways and the method further includes reconstructing the passageways to obtain a reconstructed passageway system and determining a spatial relationship between the reconstructed passageways and passageways of the passageway system in the preoperative image. In some aspects, reconstructing the passageways may include communicating localization signals between a localization system and localization sensors distributed in the passageways. The method may further include positioning the localization sensors in the passageways using one or more catheters.

In some aspects, determining the location of the SOI relative to the reconstructed passageway system may include mapping the location of the SOI relative to the passageways in the preoperative image to the reconstructed passageways. In some aspects, determining the location of the imaging device relative to the location of the reconstructed body structure includes communicating localization signals between a localization system and one or more localization sensors positioned in or on the imaging device. In some aspects, determining the location of the SOI relative to the reconstructed body structure includes obtaining localization information related to locations of localization sensors contained in the body structure and identifying a spatial relationship between the body structure in the preoperative image and the body structure containing the localization sensors.

In aspects, the method may include modifying the preoperative image according to a change in an imaging perspective of the imaging device with respect to the organ. In aspects, the change in the imaging perspective of the imaging device may include a change in distance between the imaging device and the organ or a change in an imaging angle of the imaging device. In aspects, modifying the preoperative image may include modifying a size, a shape, a proportionality, or an orientation of image content of the preoperative image. In aspects, the method may include displaying the modified preoperative image in conjunction with the intraoperative image.

In aspects, the method may include overlaying the modified preoperative image on the intraoperative image. In aspects, the method may include modifying the preoperative image such that a viewpoint of the preoperative image matches a viewpoint of the intraoperative image. In aspects, modifying the preoperative image may include aligning a viewpoint of the organ, a viewpoint of the passageway system associated with the organ, and a viewpoint of the SOI in the preoperative image with the view of the images captured by the imaging device. In aspects, the SOI includes an anatomic structure that is a diseased organ portion, a diseased lung portion, an abnormal tissue, an abnormal organ, or a benign anatomic structure. In aspects, the SOI includes one or more organ objects. In aspects, the organ is a lung, the body structure is lung airways, and the imaging device is a video camera.

In some aspects, producing the image object that represents the SOI may include imparting morphological properties (e.g., a size, a shape, and/or an orientation) of the SOI in the preoperative image to the image object. The organ subjected to the systems and methods described herein may be a lung, a liver, a kidney, a ureter, or a heart. The organ passageways may be lung airways, liver ducts, or heart blood vessels. A preoperative image may be obtained by, e.g., a medical diagnostic imaging (MDI) system. The result of imaging by an MDI system is referred to herein as an "MDI image". The terms "preoperative image" and "MDI image" are used herein interchangeably, though a preoperative image may be obtained by using other imaging systems as well.

In another aspect, a method for guiding a surgeon may include: receiving or obtaining an image of a passageway system associated with an organ including one or more passageways and a structure of interest (SOI) that resides, at least partly, in the organ; determining a location of the SOI relative to a reconstructed passageway system based on a location of the SOI relative to the passageway system in the received image; taking, by an imaging device, multiple images and, while taking the multiple images, performing, for each image of the multiple images: determining a location of the SOI relative to each image based on the location of the SOI relative to the reconstructed passageway system and a relationship between each image and the reconstructed passageway system; producing an image object that represents the SOI; and overlaying the image object on each image at the determined location of the SOI relative to each image. In aspects, producing the image object that represents the SOI may include imparting to the image object a size, a shape, and an orientation that comply with a size, a shape, and an orientation of the SOI relative to the passageway system in the received image. In aspects, the method may include modifying the received image such that a viewpoint of the received image matches a viewpoint of the multiple images. In aspects, the method may include displaying the modified preoperative image in conjunction with the multiple images.

In yet another aspect, a system may include a localization system configured to determine a location of passageways in a passageway system associated with an organ. The number of passageways in a passageway system of an organ that include localization sensors may depend on the organ which is subjected to the medical procedure. The system may further include an imaging device configured to generate a stream of intraoperative images. In some aspects, the imaging device may include one or more localization sensors to localize the imaging device by the localization system. The system may further include a controller, which may be configured to: reconstruct the passageway system based on the location of the plurality of passageways; determine, based on a preoperative image of an organ's passageway system and an SOI, a location of the SOI relative to the passageway system in the preoperative image; determine, based on the location of the SOI relative to the passageway system in the preoperative image, a location of the SOI relative to a reconstructed passageway system; take, by the imaging device, an intraoperative image; determine a location of the imaging device relative to a location of the reconstructed passageway system; and determine a location of the SOI relative to the intraoperative image based on the location of the SOI relative to the reconstructed passageway system and the determined location of the imaging device relative to the location of the reconstructed passageway system. The controller may, then, overlay, on the intraoperative image, an image object representing the SOI at the determined location of the SOI relative to the intraoperative image.

In aspects, the controller may be configured to determine the location of the SOI relative to the reconstructed passageway system by determining a spatial relationship between the reconstructed passageway system and the passageway system in the preoperative image. Reconstructing passageways may include communicating location information between the localization system and localization sensors distributed in the passageways. The localization sensors may be mounted on catheters positioned in the passageways, respectively.

In aspects, determining the location of the SOI relative to the reconstructed passageway system may include mapping the location of the SOI in the preoperative image to the reconstructed passageway system. In aspects, the location of the imaging device relative to the location of the reconstructed passageway system is determined based on location information from one or more localization sensors positioned in or on the imaging device relative to the reconstructed passageway system. In aspects, the organ may be a lung and the passageways may be lung airways. In aspects, the controller may be further configured to modify the preoperative image according to a change in a distance of the imaging device from the SOI, or according to a change in an angle at which the imaging device takes the intraoperative image; and display the modified preoperative image on a display device in conjunction with the intraoperative image. In aspects, the imaging device is a video camera.

BRIEF DESCRIPTION OF DRAWINGS

Various example aspects are illustrated in the accompanying figures with the intent that these example aspects not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding, or analogous elements. Of the accompanying figures:

FIG. 3A is a schematic diagram illustrating a preoperative image including an organ's passageways and an SOI according to an example aspect;

FIG. 3B is a schematic diagram illustrating deployment of localization sensors in passageways of or in an organ according to an example aspect;

FIG. 3C is a schematic diagram illustrating reconstructed passageways corresponding to the passageways of FIG. 3B with the SOI of FIG. 3A positioned relative to the passageways;

DETAILED DESCRIPTION

Figure 1:
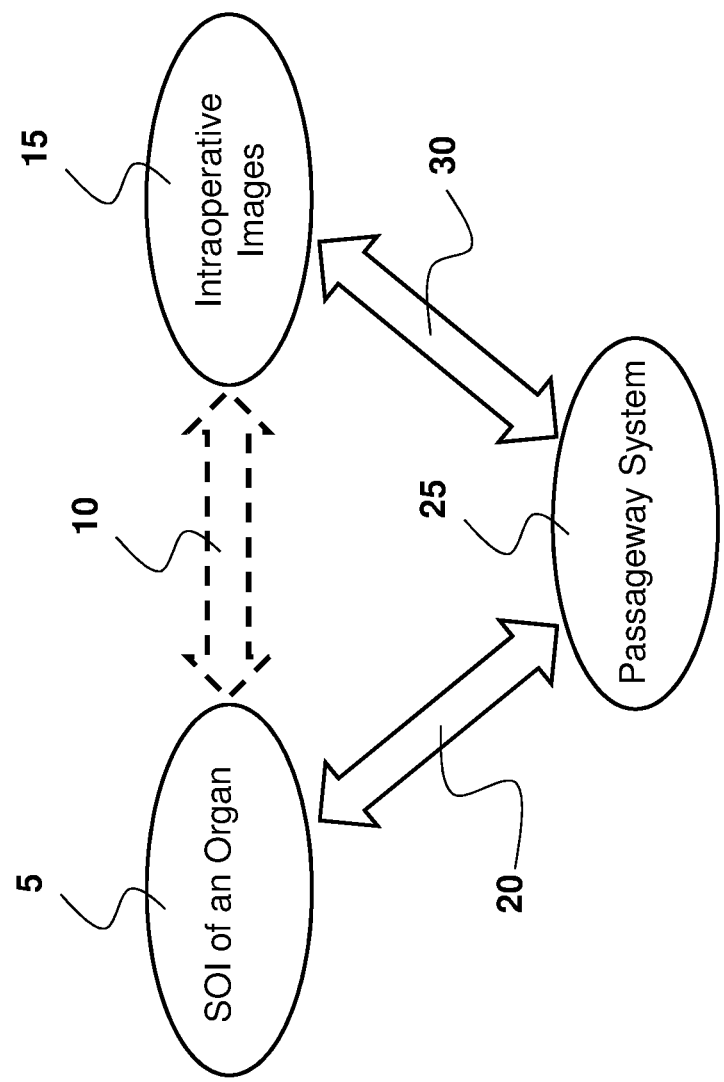
FIG. 1 is a flow diagram illustrating a method for guiding a surgeon to an SOI in an organ according to the disclosure.

The description that follows provides various details of example aspects. However, this description is not intended to limit the scope of the claims but instead to explain various principles and the manner of practicing it.

When a structure of interest (SOI) is inside an organ, the benefit of using a video camera is limited because it cannot guide or show the surgeon the location of the SOI. For example, a laparoscope enables operation on a body organ (e.g., lung) by viewing the organ from some distance (e.g., a few millimeters or a few centimeters). If a neoplasm to be removed is located inside a body organ, where it cannot be accessed through an anatomical passageway (e.g., an airway, blood vessel, etc.) or through natural orifices, laparoscopic instruments can penetrate the organ (e.g., lung) in order to reach the intended location inside the lung. However, the video camera may not be able to follow into the lung because the video camera would be occluded by blood, fat, tissues, etc. Thus, cutting into and through the lung, for example, under such conditions (e.g., without the surgeon knowing what she is going to cut beneath the surface of the lung) may result in a trial-and-error-like surgery process, which puts healthy or sensitive tissues or critical structures (e.g., nerves, blood vessels, the heart etc.) at risk and may result in the infliction of massive bleeding. This could be avoided if the surgeon knew the exact location of the portion of the lung that is the subject of the laparoscopic surgical procedure and/or the exact location of a critical structure adjacent to that portion of the lung.

It would, therefore, be beneficial to have surgical systems and methods that would enable a surgeon to operate on an SOI inside a body organ (for example, to operate on a portion of the lungs inside the lungs) by using laparoscopic surgery while enabling the surgeon to know (e.g., to see) the exact location of the SOI, while minimizing the risk of damaging other, nearby, anatomical structures, for example, healthy or sensitive anatomical structures, during the surgical procedure. As used herein, the terms lung, airway, and diseased lung portion (DLP) are, respectively, examples of an organ, a passageway, and a diseased organ portion (DOP). DLP and DOP are example anatomical SOIs.

In laparoscopic surgery, for example, a video camera captures only that which is in front of the video camera. Thus, the user may not see an SOI in the video images captured by the video camera because the SOI may be located inside an organ while the video camera may be located outside of the organ. In addition, the user may not see critical structures, which may be located nearby (e.g., other organs or blood vessels), in the video images. The systems and methods of this disclosure detect or determine the location of unseen SOIs (e.g., targets and/or critical structures) with respect to the two-dimensional video images captured by the video camera and add information regarding the unseen SOIs to the captured video images in real time. The information regarding the unseen SOIs may be added to the video images by combining the information with the video images (e.g., augmentation) or by overlaying, covering, or replacing the video images with information or data indicating the location of an SOI. As used herein, the term "capturing images" may include receiving, acquiring, or recording images, or the process of taking image data, e.g., frames of video images, from an image sensor of an electronic imaging device, e.g., a video camera.

To add information regarding the unseen SOIs to video images, the location of the SOI with respect to the video camera needs to be determined in real time. The systems and methods of this disclosure use a body structure, e.g., the airways of the lung, and preoperative images of the SOI to determine the location of the video camera with respect to the body structure and the location of the SOI with respect to the body structure. Then, the location of the SOI is determined with respect to the video camera via the body structure.

The position of the body structure and the position and orientation of the video camera may be determined by placing localization or location sensors in and/or on the body structure and the video camera. For example, EM sensors may be placed in airways of a lung via electromagnetic navigation bronchoscopy (ENB) and anchored to the airways. Accordingly, the structure of the airways may be constructed in real time and the location of the video camera with respect to the constructed airways may be determined in real time. The location of the SOI with respect to the body structure (e.g., airways of a lung) is also determined. This may be performed by using preoperative 3D images, which capture an entire area, e.g., a CT scan. The location of the SOI with respect to the body structure may be determined from the preoperative 3D images. Then, the constructed body structure is aligned with the preoperative 3D images to determine a location of the SOI with respect to the constructed body structure.

In some aspects, it is assumed that the SOI moves together with the body structure. As a result, the SOI and the body structure may need to be located near or adjacent to each other (e.g., in the same organ or anatomic region, e.g., a lung). In other aspects, the SOI and the body structure may be located in regions which do not move together. In those aspects, a model or other way may be used to determine the movement of the SOI relative to the body structure. In aspects, the systems and methods of this disclosure may be applied to imaging technologies other than video cameras (e.g., spectral cameras) to allow for the display of body structures which may not be visible using the other imaging technologies.

FIG. 1 shows a simplified diagram that explains the methods of the disclosure. A goal of the disclosure is to overlay (e.g., via registration 10) an image, which represents one or more SOIs that reside, at least partly, in one or more organs, (e.g., an SOI of an organ 5) in a correct location relative to intraoperative images (e.g., video camera images of the organ 15), in order to guide a surgeon when she cuts through the one or more organs to reach the one or more concealed or partly concealed SOIs or to an area adjacent to the one or more concealed or partly concealed SOIs. However, since the one or more SOIs are inside or partially inside (concealed in or partially concealed in) the one or more organs that are to be operated on, the one or more SOIs are invisible both to the surgeon and to the video camera. The video camera takes or captures red-green-blue (RGB) images or pictures of the organ from a distance. This problem is circumvented, according to the disclosure, by using the organ's inherent anatomic passageway system (e.g., passageway system 25) as a "registration intermediator". The description of FIG. 1 below refers to one SOI, but if there is more than one SOI, the registration process described herein is applied to all SOIs; that is, every SOI may be processed in the same way.

The process of overlaying (e.g., via registration 10) an image object representing an SOI of an organ 5 in a correct location relative to intraoperative images 15 of the organ includes a phase of registering (e.g., via registration 20) the SOI image object to preoperative images of the organ's inherent anatomical passageway system 25, and another phase of registering (e.g., via registration 30) intraoperative images 15 of the organ to the same organ's inherent passageway system 15. Since the organ's passageway system 15 is inside or adjacent to the organ, the organ's passageway system 15 may be concealed by the organ. Thus, the organ may be invisible both to the surgeon and to an imaging device, such as a video camera (e.g., an RGB camera).

According to the disclosure, the organ's passageway system is synthesized, reconstructed, or reproduced, wholly or partly, for example, by distributing localization sensors along the length of one or more of the organ's passageways (e.g., by inserting a catheter having multiple localization sensors distributed along all or a portion of the catheter's length), and processing localization information that is obtained from, or using, the localization sensors. In other aspects, the organ's passageway system is reconstructed by moving a catheter having a localization sensor through one or more of the organ's passageways, obtaining localization information at multiple timepoints as the catheter moves through one or more of the organ's passageways, and then processing the localization information. A localization sensor may be or may include a transducer that is configured to sense one or more localization signals that originate from another device or system, and to output a location signal or location data, by which the location of the localization sensor may be determined. A localization sensor may be configured to transmit localization signals to an external device or system in order for the external device or system to determine the location of the localization sensor. A passageway or an airway that includes at least one localization sensor are respectively referred to herein as a "sensorized passageway" or a "sensorized airway".

The actual organ's passageways/airways and the actual organ's passageway/airway system, which are subjected to the passageways/airways reconstruction process, are respectively referred to herein as "actual passageways/airways" and "an actual passageway/airway system". Since the spatial, three-dimensional (3D) size, shape, and proportionality of the reconstructed passageways/airways in a passageway/airway system are determined by using location information that is obtained from localization sensors that are distributed in actual passageways/airways, the reconstructed or estimated passageways/airways resemble the actual passageways/airways in size, shape, and proportionality. Therefore, registration between an SOI and reconstructed passageways/airways is equivalent or similar to registration between the SOI and the actual passageways or airways, and registration between an intraoperative image and the reconstructed passageways/airways is equivalent or similar to registration between the intraoperative image and the actual passageways/airways.

The SOI-to-organ passageways registration 20 and the intraoperative images-to-organ passageways registration 30 are ultimately used to perform registration 10, which is between the SOI's object image and the intraoperative images. The notion behind the three-step registration process is that if a first spatial relationship between an SOI and body passageways and a second spatial relationship between the body passageways and an intraoperative image are known (e.g., are measurable), then a third spatial relationship between the SOI and the intraoperative image can be obtained, inferred, deduced, and/or calculated from the first and second spatial relationships.

A method for intraoperatively guiding a surgeon to an SOI inside an organ may include, in accordance with an example aspect of the disclosure, determining (e.g., by a controller) the locations of (1) one or more passageways of an organ and (2) one or more SOIs related to (e.g., of or inside) the organ, which are included or shown in one or more preoperative medical diagnostic imaging (MDI) images of an organ. The method may further include determining (e.g., by the controller) the locations of the one or more SOIs relative to the one or more passageways of the organ based on the locations of the one or more SOIs and the one or more passageways shown in the one or more preoperative MDI images.

The method may further include taking or capturing a video stream including a series of subsequent video images (e.g., intraoperative images) of the organ or a portion of the organ by a video camera, and, while taking or capturing the video stream, co-aligning, by the controller, each video image with the organ's passageways; determining, by the controller, a location of the SOI relative to the intraoperative image based on the location of the SOI relative to the organ's passageways and the alignment between the video image and the one or more preoperative MDI images showing the organ's passageways; and generating and overlaying, by the controller, an image object representing the SOI on the video image at the determined location of the SOI relative to the intraoperative image. Overlaying the image object representing the SOI on the video image at the determined location may include displaying the video image with the SOI image object overlaid (e.g., superimposed) on the image at the determined location so that a surgeon knows where the organ's SOI is relative to the intraoperative image.

In some aspects, determining the location of the SOI relative to the organ passageways may include reconstructing organ passageways and aligning the resulting reconstructed passageways to the video image passageways. Reconstructing the organ passageways may be based on localization signals that may be exchanged between a localization system and a plurality of localization sensors that are distributed along the length of one or more organ passageways.

Aligning the intraoperative image and the reconstructed organ passageways may include exchanging localization signals between a localization system and at least one localization sensor that is positioned in the video camera (e.g., at the tip, or distal end, of the video camera). Positioning two localization sensors in a video camera may enable a controller to determine the spatial angle of the video camera's line of sight, for example, relative to the body organ that is operated on, and relative to the expected location of the SOI. The video camera's spatial angle feature may enhance the surgeon's orientation in the surgery site.

The organ may be, for example, a left or right lung, and the organ passageways may be, for example, lung airways.

In some aspects, determining the location of the SOI relative to the organ passageways may include determining a spatial relationship between the passageways in the MDI image and the reconstructed passageways, and mapping the location of the SOI in the MDI image relative to the reconstructed passageway system at a similar or identical location. Determining the location of the SOI relative to the passageway system may include obtaining localization information related to location of localization sensors contained in the passageway system, and identifying a spatial relationship between passageways in the preoperative image (in the MDI image) and passageways containing the localization sensors.

Figure 2A:
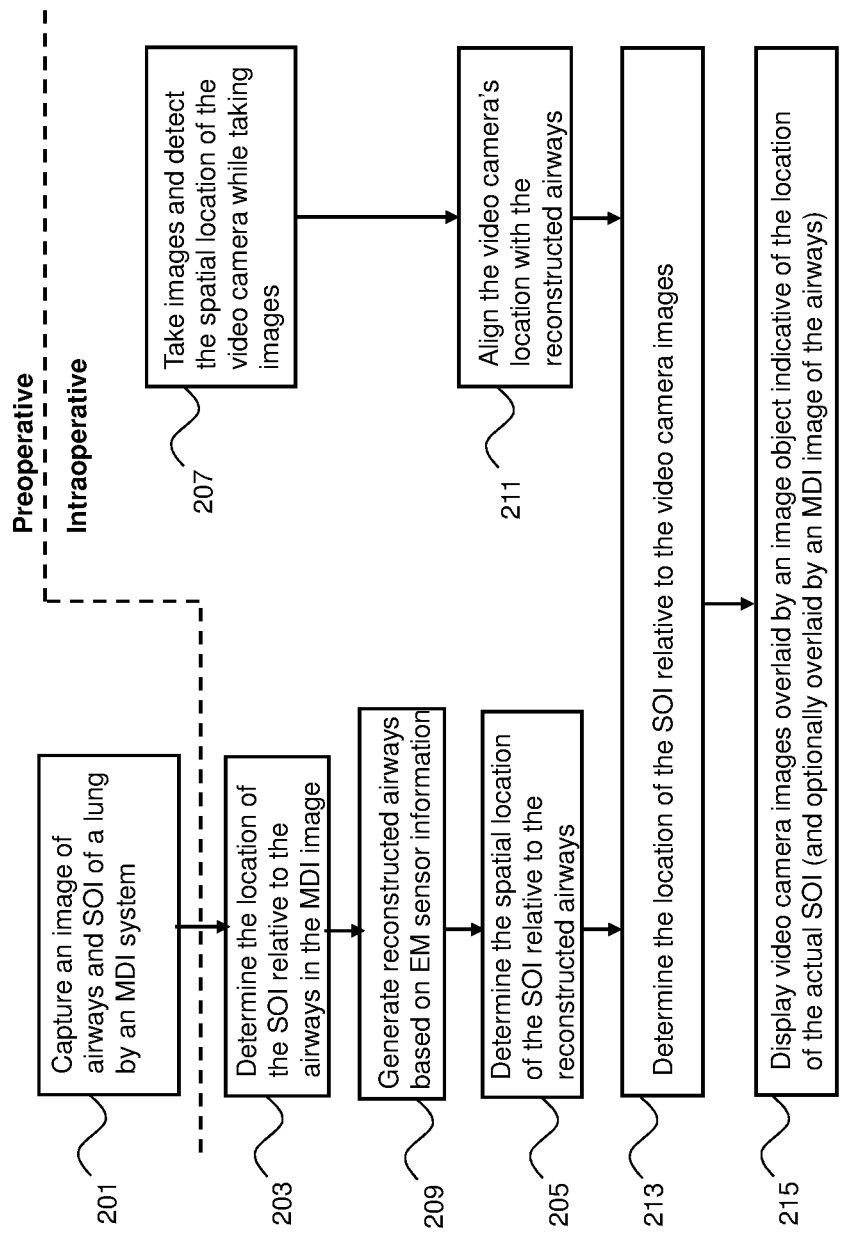
FIG. 2A is a flow diagram illustrating a method for guiding a surgeon to an SOI in an organ according to an example aspect.

FIG. 2A shows a method for guiding a surgeon to an SOI in an organ according to an example aspect. FIG. 2A describes the method in connection with lung and lung airways; however, the same or similar method may be applied to any other organ, for example, the heart, liver, stomach, cardiovascular system, etc. A similar method may be used to guide a surgeon during any surgical procedure in which localization sensors can be fixedly deployed in a passageway system of an organ during the surgical procedure.

The method may include two main phases: (1) a preoperative phase, and (2) an intraoperative phase. In the preoperative phase, for example at step 201, an image of a patient's lung may be captured by an MDI system in order to capture an image showing the lung, the lung's airway (or at least of some of the lung's airways) and, in addition, an SOI, which may be a candidate anatomic structure for surgery or an anatomic structure that must not be damaged during surgery. One or more of the following steps may also be performed in the preoperative phase (e.g., steps 203 and 205). After the image of the patient's lung is captured, the lung, the lung's airway, and the SOI may be identified in the image of the patient's lung. For example, the lung, the lung's airway, and the SOI may be marked, e.g., by a clinician or by an image recognition or segmentation algorithm, in the image of the patient's lung.

At step 203, the location of the SOI (e.g., a diseased lung portion (DLP)) and the lung's airways as imaged by the medical diagnostic imaging (MDI) system may be determined (e.g., by a controller). For example, a reference frame (e.g., the Cartesian coordinate system) may be used to locate the SOI and the airways so that the location of the SOI relative to the airways in the MDI image may be determined, for example, by a computer system, as described below with respect to step 205. A set of images of the lung may be acquired by the MDI system (for example, by a computerized tomography (CT) system) before surgery is performed or in preparation for the surgery. The type of MDI system that is used may be selected such that images captured by the MDI system can clearly distinguish (e.g., visually) (1) the SOI (e.g., a malignant or benign tumor) that needs, for example, to be resected (e.g., ablated), and (2) at least some of the airways or other anatomical passageways of the lung. In an example aspect, in terms of fiducial indicia, at least one airway in the lung may be distinguishable, e.g., by being visible or detectable in the MDI images. One or more discernible airways or other anatomical passageways in the lung can be used as a basis for indicating an estimated location of the SOI on intraoperative images of the lung (e.g., by overlaying an image object on intraoperative images of the lung) in order to provide guidance to the surgeon during the surgical procedure.

At step 209, reconstructed airways are generated based on EM sensor information received or obtained from, e.g., one or more localization sensors described herein. At step 205, the spatial location of the SOI relative to reconstructed or synthesized airways is determined. The spatial location of the SOI relative to the reconstructed airways may be found using the location of the SOI in the one or more MDI images relative to the location of the airways in the one or more MDI images.

The spatial location of the lung airway system may be determined by distributing localization sensors along the length of the lung airways of the lung airway system; transmitting localization signals (e.g., electromagnetic signals) between the localization sensors fixedly positioned along the length of the airways and an external localization system (e.g., electromagnetic localization system); and determining the spatial location, shape, and size (e.g., length) etc. of these airways based on the location information that is obtained from or using the localization sensors. The shape of each lung airway that contains localization sensors may then be reconstructed or reproduced (e.g., mathematically and, optionally, also visually) based on, or from, the spatial location information obtained from the localization sensors. In other aspects, a localization sensor may be swept or moved through the lung airways to obtain spatial location information, which may be used to reconstruct or reproduce the shape of the lung airways.

Some characteristics of the internal anatomy or structure of the lung are common medical knowledge, such as the airways' diameters (e.g., for a patient of a particular size and at a particular time in the respiration cycle) and the main structure of the airways tree. Such knowledge may help to anatomically identify airways in the MDI image, and to associate the actual airways with corresponding reconstructed airways in the organ's airway system. After each reconstructed airway (or after a reconstructed airway system) is anatomically identified, it can be correlated, for example, based on physical shape and/or anatomical functionality, to a corresponding airway or airway system shown in the MDI image. The correlation process may result in alignment between the reconstructed airways or reconstructed airway system to the respective airways or airway system shown in the MDI image. Spatially aligning an MDI image and an intraoperative image may include spatially matching passageways appearing in the MDI image to an intraoperative image based on the location of the localization sensors. That is, when localization sensors are disposed in a passageway system, the locations of the localization sensors can fit the structurally nonrecurring three-dimensional anatomy of the passageway system of the anatomic organ in one way. So, having prior medical knowledge of the anatomy of the passageway system of the anatomic organ enables a computer system to know which passageways of the passageway system contain the localization sensors and to align the image content of the MDI image and the image content of images.

Once the reconstructed airways/passageways or airway/passageway system are spatially aligned with the airways or the airway system in the MDI image, the spatial location of the SOI relative to the reconstructed airways (in the reconstructed airway system) may be determined, at step 205, from, or based on, the location of the SOI in the MDI image relative to the corresponding airways or airway system in the MDI image. In other words, the position of the SOI relative to the reconstructed airways should match or correspond to the position of the SOI relative to the airways in the MDI image. Since each reconstructed airway spatially represents a particular airway, determining a location of the SOI relative to a reconstructed airway is analogous to determining the location of the SOI relative to the relevant airway as imaged in the pre-procedure phase.

At step 207, images are taken by an endoscopic video camera that may include one or more localization sensors, and a two-dimensional (2D) location (or a three-dimensional (3D) location) of the video camera may be detected, for example, by a localization system while images of the surgery site are taken. The video camera outputs a stream of images of, for example, the lung while the surgical procedure is in progress. The one or more localization sensors of the video camera may be affixed, or removably attached, to, for example, a distal end, section, or tip of an endoscope.

At step 211, the video camera's location and the reconstructed airways are co-aligned. Since both the location of the SOI and the position of the video camera (and hence the relative orientation of images captured by the video camera) are determined (at steps 205 and 211, respectively) relative to the same reconstructed airways, the location of the SOI may be also determined relative to the images captured by the video camera, at step 213.

At step 215, a controller or a computer system executing the method may display images captured by the video camera, for example, on a computer screen or display, with an image object, which may figuratively represent the SOI, displayed at a location corresponding to, or coinciding with, the location of the SOI in the MDI image of the lung.

Figure 2B:
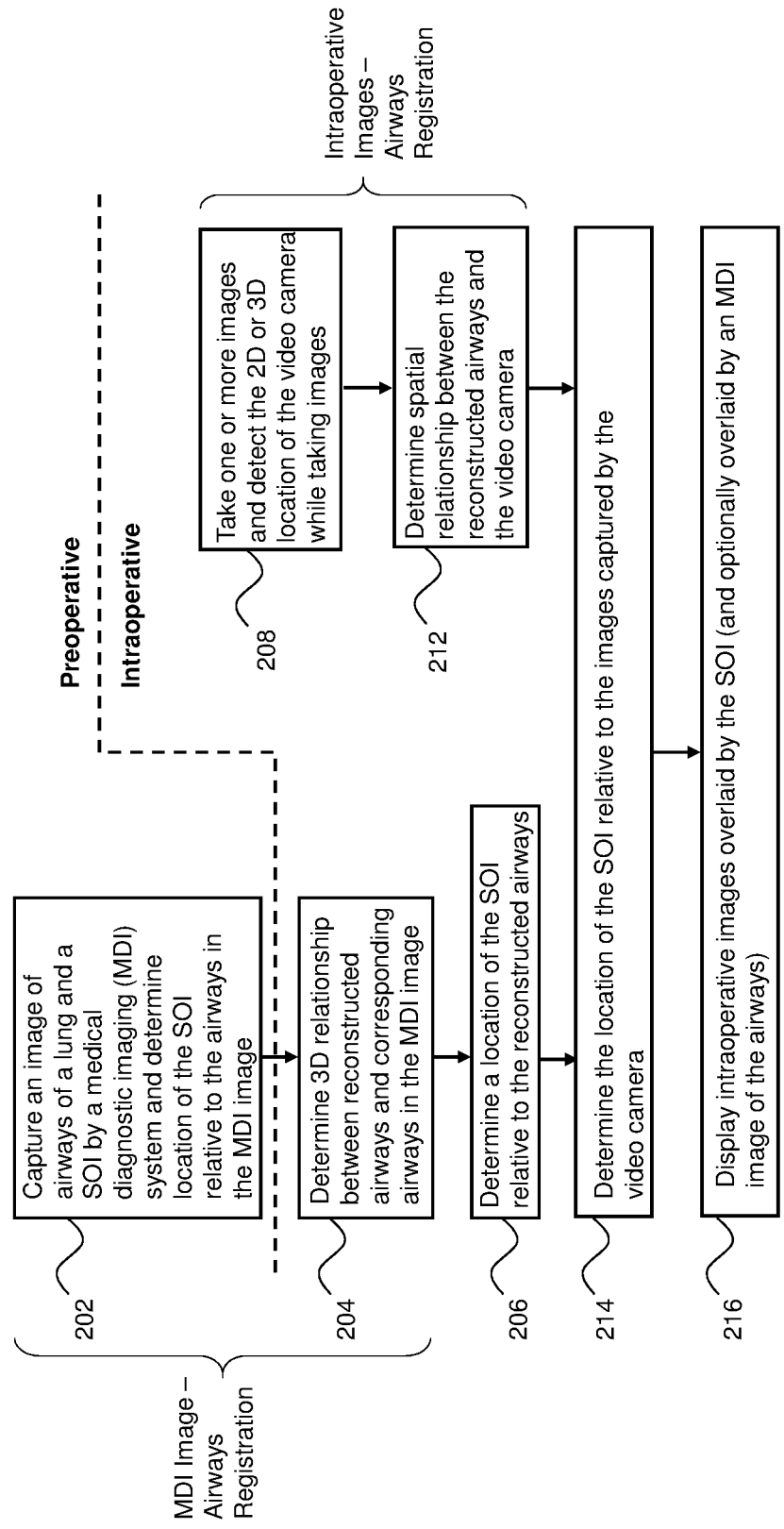
FIG. 2B is a flow diagram illustrating a method for guiding a surgeon to an SOI in an organ according to another example aspect.

The example method shown in FIG. 2B performs two registrations: (1) "MDI image-to-airways" registration (executed at steps 202 and 204), and (2) "intraoperative image-to-airways" registration (executed at steps 208 and 212). Steps 204 and 206 are performed sequentially and steps 208 and 212 are performed sequentially. Steps 204 and 206 and steps 208 and 212 may generally be performed in parallel.

FIG. 2B shows a method for providing guidance to a surgeon during pulmonary thoracic surgery according to an example aspect. The method includes two main phases: (1) a preoperative phase, and (2) an intraoperative phase. In the preoperative phase, for example at step 202, an image of a patient's diseased lung is acquired or captured by an MDI system in order to capture an image of some or all the lung's airways and an SOI. Also, the location of the SOI is determined, for example, at step 202, or at any other suitable step (e.g., when this kind of information is needed for further processing or calculation) relative to the MDI-imaged airways.

At step 204, a spatial, three-dimensional relationship between reconstructed airways and the MDI image of airways (that is, airways seen or detectable in the lung as seen in the MDI image) is determined. The step of spatially determining the relationship between reconstructed airways and the airways in the MDI image may include a step of aligning the two types of airway information, for example, by aligning the reconstructed airways and the corresponding MDI image of the airways.

Once the reconstructed or synthesized airways or airway structures are aligned with the airways or airway structures in the MDI image, the spatial location of the SOI relative to the reconstructed airways or airway structures is determined, at step 206, from or based on the MDI image. That is, the spatial location of the SOI relative to the reconstructed airways or airway structures is determined from or based on the location of the SOI in the MDI image relative to the corresponding, matching, or associated airways or airway structures in the MDI image. In other words, the position of the SOI relative to the reproduced airways should match or substantially match the position of the SOI relative to the airways or airway structures in the MDI image.

At step 208, images are taken by an endoscopic video camera, which may include one or more localization sensors, and a two-dimensional (2D) location or a three-dimensional (3D) location of the video camera is detected, for example, by a localization system while images are taken by the endoscopic video camera. The video camera may output a stream of images (e.g., video images) of the lung while the surgical procedure is in progress. The localization sensors of the video camera may be affixed, or removably attached, to a distal end, section, or tip of an endoscope carrying the video camera.

At step 212, the 2D or 3D location of the video camera relative to the reproduced airways is determined. Since both the location of the SOI and the position of the video camera (and hence the images captured by the video camera) are determined (at steps 206 and 212, respectively) relative to the same reconstructed airways, the location of the SOI may be also determined, at step 214, relative to the images captured by the video camera. The location of the video camera relative to the reconstructed airways may be monitored while and as long as the video camera is operated, and the surgical procedure is in progress. At step 216, an image object representing the SOI (and, optionally, also an image of the airway system) may be overlaid on the images at the respective locations with respect to the images, thus producing a complex image, and the complex image may be displayed, for example, on a computer screen or on a television set.

The method sown in FIG. 2B performs two registrations: (1) MDI image—airways registration (executed at steps 202 and 204), and (2) Intraoperative image—airways registration (executed at steps 208 and 212). Steps 204 and 206 are performed sequentially, as are steps 208 and 212. Steps 204 and 206 may generally be performed in parallel with steps 208 and 212.

Figure 2C:
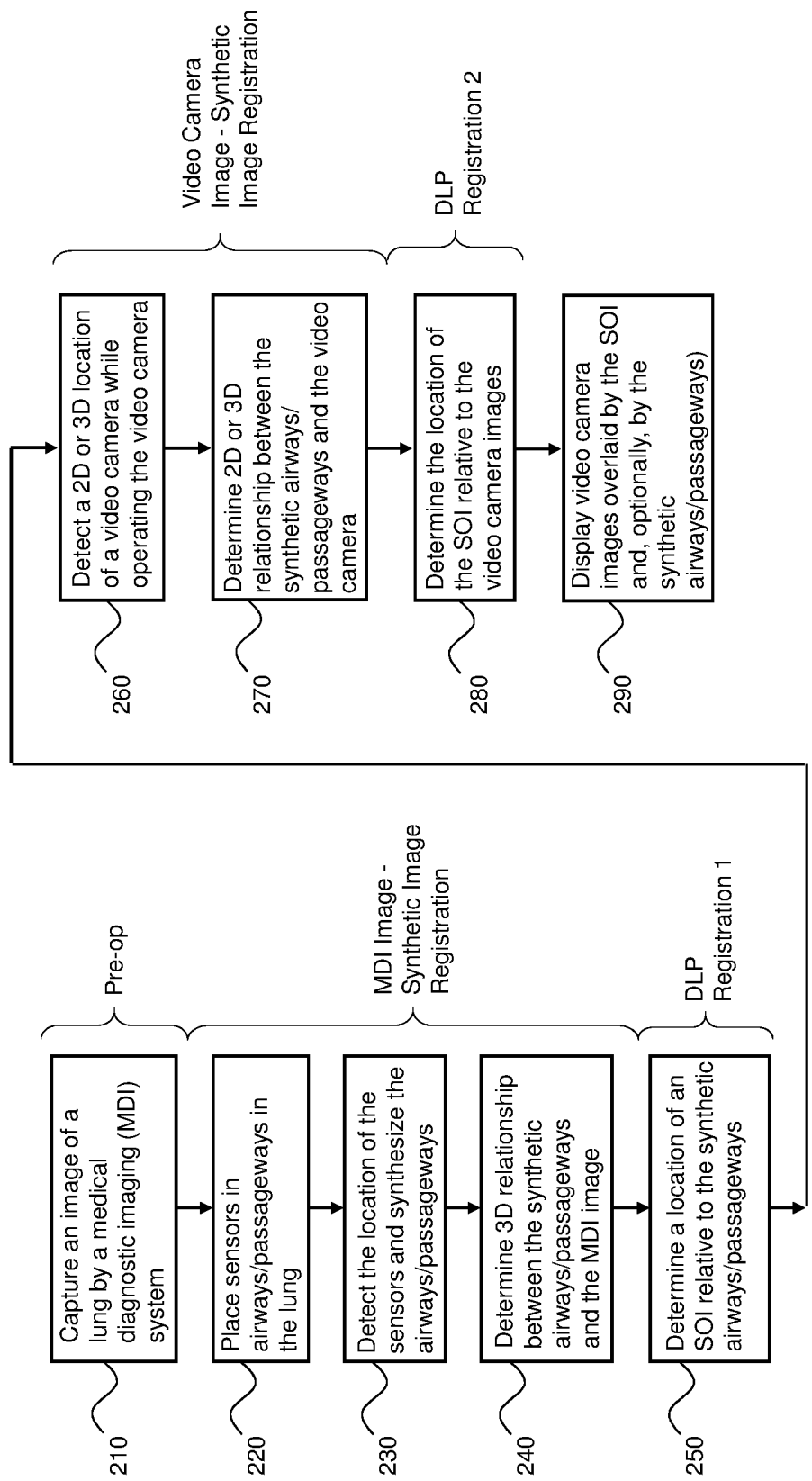
FIG. 2C is a flow diagram illustrating a method for guiding a surgeon to an SOI in an organ according to yet another example aspect.

FIG. 2C shows a method for guiding a surgeon to a surgery site during pulmonary surgery according to an example aspect. At step 210, a set of images of a lung including an SOI is acquired by an MDI system, for example, before surgery is performed.

Step 210 may also include a step of determining, from the set of MDI images, a spatial, 3D location (for example, {x,y,z} location) of the SOI relative to airways or passageways in the lung that are discernible in the MDI images. During scanning of an organ, MDI systems may take multiple images of the organ, where each image depicts a different "slice" of the organ, and three-dimensional information (e.g., a 3D model) of the organ may be obtained from a series of subsequent slices. While each image slice shows a planar image of the organ (e.g., in the {X, Y} plane), the set of image slices (e.g., CT image slices) add the organ's third dimension (e.g., in the Z direction, to maintain consistency with respect to the example {X, Y} plane). Therefore, the location, shape, size, and spatial orientation of every object that is discernible (e.g., visible) in the set of image slices can be determined (e.g., calculated) relative to the location, shape, size, and spatial orientation of every other object that is discernible in the set of image slices.

At step 220, a set of localization sensors (for example, magnetic field sensing transducers) are placed or distributed in one or more of the lung's airways. The set of localization sensors are placed or distributed in one or more of the lung's airways that are discernible (e.g., visually) in the MDI images. Placing localization sensors in this manner enables, for example, a controller to register the MDI image content, in particular the SOI and the lung airways, in which the localization sensors reside during surgery, to the airways as sensed, for example, by the localization system, in real-time during the surgical procedure. The localization sensors, which are lengthwise distributed in lung airways that are visually discernible in the MDI image and which can be sensed by the localization system during the surgical procedure, enable, for example, a controller or a computer system, to reconstruct (image-wise) the airways accommodating the localization sensors, and, optionally, to generate a synthetic image showing some or all of the reconstructed airways, in addition to other image objects.

A synthetic image, which may be a two-dimensional (2D) image or a three-dimensional (3D) image, is a computer-generated image that may include an image object that figuratively and morphologically represents the reconstructed airways that contain localization sensors, or multiple image objects where each image object figuratively and morphologically represents one reconstructed airway. The synthetic image may also include an image object that figuratively and morphologically represents the SOI. The synthetic image may include an image object that figuratively and morphologically represents both the reconstructed airways and the SOI. Reconstruction of lung airways may include producing, by a controller or computer system, image objects that figuratively represent the sensorized lung airways.

In some aspects, a lung airway that is not sensorized is not reconstructed; therefore, such an airway may be excluded from the synthetic or reconstructed image. However, as described herein, at least the general anatomy and functionality of the passageway system are common medical knowledge. By using such medical knowledge, the spatial position of an un-sensorized airway, for example, may be interpolated from reconstructed airways. Interpolated airways, when jointly used with reconstructed airways, may enhance the accuracy with which the location of the SOI relative to the reconstructed airways and, hence, relative to the intraoperative images is determined.

The localization sensors may be placed in some of the lung airways (for example, in the patient's bronchial tree), for example, by being inserted through natural body orifices and into the lung's airways (e.g., airways in a lung segment or lobe to be operated on) by a catheter. Multiple localization sensors may be lengthwise disposed in or on a catheter. One or more catheters carrying one or more localization sensors may be inserted into one or more of the lung airways in order to facilitate reconstruction of the sensorized lung airways. The one or more catheters carrying the one or more localization sensors may be inserted into lung airways and attached to the lung airways throughout the surgical procedure. Attaching a catheter to an airway may be performed, for example, by using a balloon, a clip, or any other suitable attachment mechanism.

One or more catheters including localization sensors may be inserted into lung airways through, for example, a working channel of a bronchoscope. Catheters including localization sensors may optionally be inserted into lung airways through a working channel of a double-lumen endotracheal tube (DLT). A DLT is a type of endotracheal tube which is used in tracheal intubation during thoracic surgery and other medical conditions to achieve selective, one-sided ventilation of either the right hand or the left lung. A DLT includes two small-lumen endotracheal tubes of unequal length that are fixed together side by side. The shorter tube ends in the trachea while the longer tube is placed in either the left bronchus or the right bronchus in order to selectively ventilate the left lung or the right lung, respectively. Catheters may be inserted into the lung airway system one catheter at a time. Alternatively, multiple catheters may be inserted into the lung through the same DLT tube (e.g., a leading channel) at the same time, and each catheter may then be navigated to a different airway.

A catheter may be navigated to a particular airway in the lung by using an electromagnetic navigation bronchoscopy (ENB) procedure, which is a minimally invasive approach that enables accessing difficult-to-reach areas of the lung and aiding in the diagnosis of lung disease. Regardless of how a catheter is inserted into any airway or passageway, the catheter may, when in the correct position, be anchored to the airway or passageway by using any suitable means, for example, a balloon, a hook, anchoring arms, etc.

At step 230, a 3D location (determined, for example, by using $\{X, Y, Z\}$ coordinates) of each sensor may be detected by an external or ex-vivo localization system (for example, an external magnetic localization system). Spatial particulars or parameters, such as the 3D shape, size, location, and orientation of each sensorized lung airway may be determined, for example, based on the 3D location of the sensors, and each particular lung airway may be reconstructed based on the spatial particulars or parameters pertaining to the particular lung airway.

Since the reconstructed lung airways are obtained by using localization sensors that are lengthwise distributed in the airways that are or were previously subjected to the imaging by the MDI system, the reconstructed airways and the corresponding MDI-imaged airways are morphologically similar. For example, they may be similar in shape, proportion, relative position, angular relationships, etc. The resemblance between the reconstructed airways and the MDI-imaged airways is a result of the fact that the same physical airway system is scanned (e.g., preoperatively) by the MDI system and is reconstructed by using location information that is obtained from or by using localization sensors.

At step 240, the reconstructed airway system and the MDI image (e.g., a CT image), which include at least part of the airway system and the SOI, may be spatially co-aligned, for example, mathematically and/or visually, in order to enable a controller or a computer system to use the same coordinate system for both types of airways, namely, the reconstructed airways and airways shown in the MDI image). Co-aligning the reconstructed airways and the related airways as imaged by the MDI system may include a step of resizing one type of airway relative to the other (for example, downsizing the reconstructed airways relative to the airways imaged by the MDI system) and spatially aligning the two types of airways. In aspects, spatial alignment of the two types of airways need not be done pictorially; this can be done mathematically. Co-aligning the reconstructed airways and the related airways imaged by the MDI system, or determining the spatial relationship between the two types of airways, is beneficial because this enables a controller to produce and position (e.g., visually) an image object, which represents the SOI, at a proper location relative to the reconstructed airway system, which corresponds to the location of the SOI relative to the airway system shown in the MDI image.

Preoperative MDI images show the lung airways at some static condition. However, the airways, which are reconstructed in real-time during a surgical procedure, may deform due to, for example, movement of the patient and/or the lung. In addition, the patient's airways may be imaged by an MDI system while the lung functions normally (e.g., such as when the patient is awake), whereas the reconstructed airways are reconstructed during the surgical procedure while the patient is anesthetized, and the lung subject to the medical procedure is collapsed, causing some or all of the airways to deform. Therefore, there may be some differences or mismatches between the MDI-imaged airways and the deformed reconstructed airways. However, since the two types of airways originate from the same physical anatomical structure (e.g., from the same bronchial tree), there may be enough resemblance (e.g., in shape, size, proportions, angles, and/or lengths) between the two types of airways to enable a controller or a computer system to co-align the airways shown in the MDI image with the deformed reconstructed airways.

Steps 220-240 embody a first registration stage (e.g., MDI image—reconstructed image registration), in which the airways image captured at step 210 by the MDI system, and the reconstructed airways, which are obtained at step 230, are co-registered, with the result of the registration process being that the location of the SOI, which may require resection or protection from being accidently cut or otherwise damaged, can be spatially determined relative to the reconstructed airways. That is, knowing the location of the SOI relative to the airways in the MDI image, and, in addition, the spatial relationship between the airways as imaged by the MDI system and the reconstructed airways, a location of the SOI may be determined (e.g., by a controller or computer system), at step 250, relative to the reconstructed airways. While the location of the SOI relative to the airways imaged by the MDI system is determined from one or more MDI images, the location of the SOI in the MDI image relative to the reconstructed airways is determined by using spatial associations between the airways shown in the MDI images and the reconstructed airways.

At step 260, a two-dimensional (2D) or three-dimensional (3D) location of an endoscopic video camera including one or more localization sensors is detected. The video camera outputs a stream of images of the lung while the surgical procedure is in progress. The one or more localization sensors of the video camera may be affixed or removably attached to, for example, a distal end, section, or tip of an endoscope carrying the video camera's optical fiber.

At step 270, the location of the video camera is used to determine the 2D or 3D relationship between the video camera and the reconstructed airways. Since the location of the diseased lung portion is determined, at step 250, relative to the reconstructed airways, and, at step 270, the video camera's position (and hence the images captured by the video camera) is determined relative to the same reconstructed airways, the location of the SOI may also be determined, at step 280, relative to the images captured by the video camera. The location of the video camera relative to the reconstructed airways may be monitored as long as the video camera is operated, and the surgical procedure is in progress.

Steps 260 and 270 embody a second registration stage (video camera image-synthetic image registration) in which (1) the location of the video camera, which is detected at step 260, and (2) the airways reconstructed at step 230 are co-registered. The result of the video camera image-synthetic image registration process is that the spatial relationship between video camera images and the reconstructed airways can also be determined and be displayed on a display screen (e.g., on a thoracoscopic view on the display screen).

At step 290, images of the lung subjected to the surgical procedure may be displayed, for example, on a computer screen, in a way that the SOI and, optionally, the reconstructed airways are overlaid (e.g., superimposed) on the video camera images. The reconstructed airways may be used by the surgeon, for example, as a reference/guiding frame to enhance surgery precision and efficacy. This way, for example, the surgeon may look at the computer display or screen and view an image object that represents in real-time (substantially at any time during the surgery) the location of the SOI relative to the video camera images, thus eliminating the need for the surgeon to guess the exact location of the SOI.

As the surgeon moves the video camera (e.g., laterally) from one point in the surgery site to another, changes the video camera's distance from the surgery site, or changes the angle of the video camera's line of sight relative to the surgery scene, the video camera's new location angle and/or distance may be continually sensed by the external localization system and subsequent video camera images may visually be readjusted (e.g., rescaled, deformed, etc.) relative to the reconstructed airways according to the video camera's changing field of view (FOV), location, angle, and distance, so as to maintain alignment, relativeness, and proportionality between the video camera images and the reconstructed airways.

For example, if the video camera is moved in some direction by some amount (e.g., five centimeters to the left), the reconstructed airways will be repositioned in the video camera images (e.g., they will be translated) in the opposite direction by the same amount (e.g., five centimeters to the right). In another example, if the video camera is completely moved away from the surgery site such that the FOV does not contain the surgery site, the reconstructed airways will completely disappear from the video camera images. And if the video camera is moved such that the video camera's FOV contains part of the surgery site, then, depending on the part of the surgery site captured by the video camera, some of the reconstructed airways may be included in the video camera images while other reconstructed airways may be excluded from the video camera images.

Since the location of the SOI is maintained relative to the reconstructed airways throughout the surgical procedure (because the location of the SOI, as imaged by the MDI system, relative to the airways is fixed (within some margin) regardless of the location of the video camera), the image object representing the SOI will not appear in an image if the location determined for the image object is outside the video camera's FOV.

While displaying the diseased lung portion (and optionally the reconstructed airways) overlaid (e.g., superimposed) on the video camera images, a computer-generated object representing the diseased lung portion may be produced such that it is visually, graphically, or otherwise highlighted or enhanced in order to make the location, orientation, shape, and/or size of the diseased lung portion conspicuous or more conspicuous relative to the video content of the video camera images. For example, a computer-made object representing the location, shape, and size of the diseased lung portion may include a visually conspicuous demarcation line or it may have one or more colors that are conspicuous relative to the one or more colors of the vicinity or background.

FIG. 3A schematically illustrates an example preoperative MDI image of a lung airway system 300 in accordance with the disclosure that, for the sake of simplicity, includes a simplified lung structure, for example, a bronchial tree including airways, and a diseased lung portion (DLP) 305. FIG. 3A corresponds to step 210 in FIG. 2C, in which one or more MDI images are captured and the relative location (for example, coordinates {x1, y1, z1}) of DLP 305 in lung airway system in MDI image 300 may be determined, for example, by using electro-optical properties of the MDI system (e.g., image signal gain, pixel output signals, zoom level, FOV, etc.) at the time the one or more images are captured. By way of example, the lung structure includes four junctions, designated as J1, J2, J3, and J4, and eight branches, designated as B1, B2, B3, B4, B5, B6, B7, and B8.

FIG. 3B schematically illustrates lung airway system 301 with catheters placed in some of the airways in accordance with the disclosure. Lung airway system 301 (a system including actual airways) corresponds to imaged lung airway system in MDI image 300 (a system including imaged airways). FIG. 3B corresponds to step 220 in FIG. 2C, in which three catheters 310-330 are placed in some lung airways of the lung airway system 301. The three catheters include the left-hand side catheter 310, the middle catheter 320, and the right-hand side catheter 330. Each imaged airway branch in FIG. 3A has a corresponding actual airway branch in FIG. 3B. For example, imaged airway branch B1 in FIG. 3A has a corresponding actual airway branch B1' in FIG. 3B, imaged airway branch B2 in FIG. 3A has a corresponding actual airway branch B2' in FIG. 3B, and so on.

Each catheter may have one or more localization sensors disposed thereon or therein. By way of example, catheter 310 includes six localization sensors S1, S2, S3, S4, S5, and S6; catheter 320 includes three localization sensors S21, S22, and S23; and catheter 330 includes three localization sensors S31, S32, and S33.

FIG. 3C schematically illustrates a synthetic or reconstructed image 302 that depicts synthetic or reconstructed airways that correspond to, are related to, or are derived from airways in actual lung airway system 301 of FIG. 3B. FIG. 3C corresponds to steps 230-250 in FIG. 2C, in which MDI image-to-synthetic image registration and DLP-to-synthetic airways registration occur.

The relative location of some or all of the localization sensors may be determined by using an external localization system. Localization information from the localization sensors may be used to synthesize or reconstruct the sensorized airways at step 230.

Every airway branch in lung airway system 301 in FIG. 3B that includes a sensor-carrying catheter has a corresponding synthesized or reconstructed airway branch in synthetic image 302. For example, airway branch B5' in FIG. 3B has a corresponding synthesized or reconstructed airway branch B5" in FIG. 3C, airway branch B7' in FIG. 3B has a corresponding synthesized or reconstructed airway branch B7" in FIG. 3C, and airway branch B8' in FIG. 3B has a corresponding synthesized or reconstructed airway branch B8" in FIG. 3C.

Synthesized or reconstructed catheters 310', 320', and 330' figuratively represent catheters 310, 320, and 330, respectively. And since the catheters assume the shape of the airways containing them, so do the synthesized or reconstructed catheters 310', 320', and 330' assume the shape of the airways. The 3D relationship between synthetic image 302 and MDI image 300 may be determined, per step 240, for example, by using the synthesized or reconstructed airway branches of synthetic image 302 and the airway branches of MDI image 300.

After the spatial relationship between synthetic image 302 and MDI image 300 is determined (e.g., mathematically), or after images 300 and 302 are spatially co-aligned (e.g., mathematically), a reconstructed location {x1',y1', z1'} is found in synthetic image 302 (at a location of the synthesized or reconstructed DLP 305'), which corresponds to or coincides with the location {x1,y1,z1} of DLP 305 in MDI image 300. The location of reconstructed DLP 305' may coincide with the location of DLP 305 or they may slightly differ. The location of reconstructed DLP 305' spatially relates to the synthesized or reconstructed airways in synthetic image 302 in the same or similar way that the location of the DLP 305 in MDI image 300 spatially relates to the airways in MDI image 300.

Figure 3E:
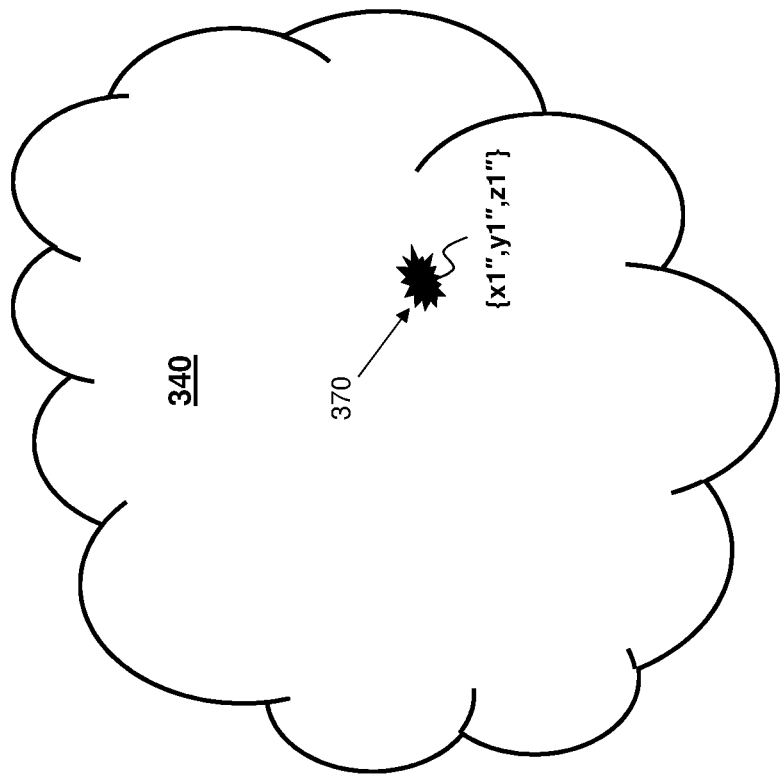
FIG. 3E is a schematic diagram illustrating the SOI of FIG. 3C overlaid on an image of a related organ according to another example aspect.
Figure 3D:
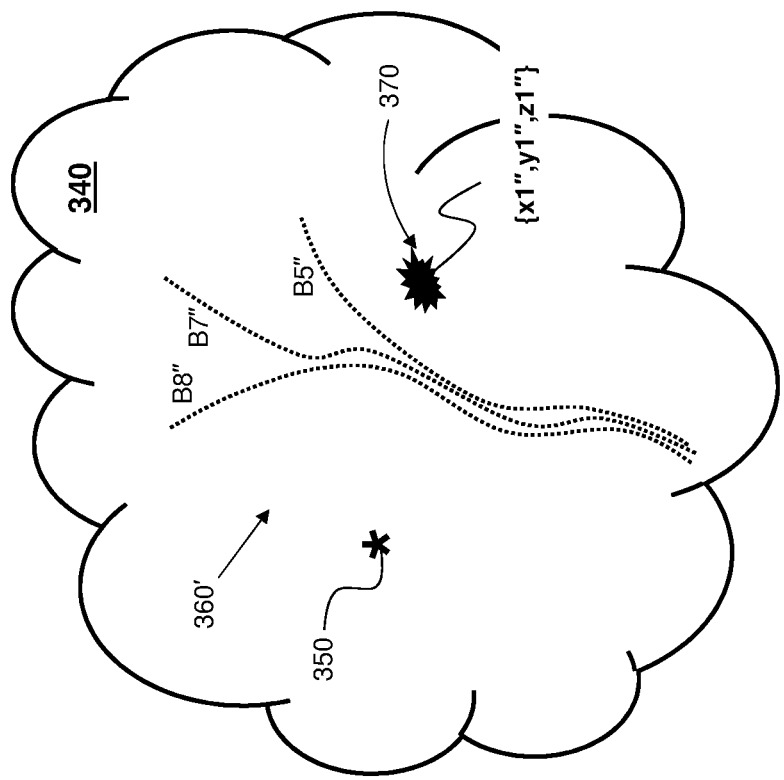
FIG. 3D is a schematic diagram illustrating the reconstructed passageways and the SOI of FIG. 3C overlaid on an image of a related organ according to an example aspect.

FIG. 3D illustrates a video camera image 340 according to an example aspect. FIG. 3D corresponds to steps 260-280 in FIG. 2C, in which video camera image-synthetic image registration and DLP second registration (registration of the DLP to the video camera images) occur. Video camera image 340 symbolically represents capturing an image of a lung undergoing surgery by a video camera at a distance from the lung.

As described herein, the video camera may include a localization sensor that enables, for example, a controller or computer system, to determine the 3D location of the video camera relative to the catheters (or catheter localization sensors). Knowing the 3D location (e.g., location 350) of the video camera relative to the catheters, and optionally knowing electro-optical parameters of the video camera, the controller or computer system may display video camera image 340 with synthesized or reconstructed airways 360' (shown in dotted lines) overlaid on video camera image 340. The controller or computer system may scale, resize, or otherwise adjust or manipulate the video camera image 340 and/or the synthesized or reconstructed airways 360' in order to maintain proportionality between them when they are displayed, for example, on a computer screen. Synthesized or reconstructed airways 360' in FIG. 3D may be a manipulated version (e.g., a rescaled version, a resized version, etc.) of synthesized or reconstructed airways 360 in FIG. 3C.

With reference to FIG. 3C, by knowing the reconstructed location {x1',y1',z1'} of reconstructed DLP 305' in synthetic image 302 relative to synthesized or reconstructed airways 360, and by performing mathematical manipulations, the controller or computer system can determine the location 370 (location {x1",y1", z1"}) of the DLP in image 340 (in FIG. 3D) relative to the manipulated reconstructed airways (i.e., relative to reconstructed airways 360'), and thus maintain all relationships/proportionality between reconstructed DLP 305', reconstructed airways 360', and video camera image 340. Reconstructed airways 360' need not be visually overlaid on video camera image 340, though reconstructed airways, if overlaid on video camera image 340, may provide additional visual guidance to the surgeon performing the surgery, for example in the form of orientation information. FIG. 3E shows video camera image 340 with the DLP at location 370.

The location of the DLP 305 relative to the video camera image 340 is determined in the way described herein. The shape and size of the DLP 305 may be determined, for example, from the one or more MDI preoperative images (e.g., one or more preoperative CT images), and be rescaled, resized, realigned, etc. with respect, or relative, to one or more video camera images in order to maintain proportionality and/or realignment with respect to the image content of the one or more video camera images. Proportionality and/or realignment between the one or more video camera images and the reproduced or synthesized airways may also be maintained in order to overlay the DLP 305 (e.g., visually) correctly (e.g., in the correct position) on the one or more video camera images as surgery progresses, thus guiding the surgeon to the right location of the DLP 305 in the lung. The guidance methods disclosed herein also enable the medical staff to use the video camera more efficiently as the surgeon cuts a way through the lung to the DLP 305.

Figure 4:
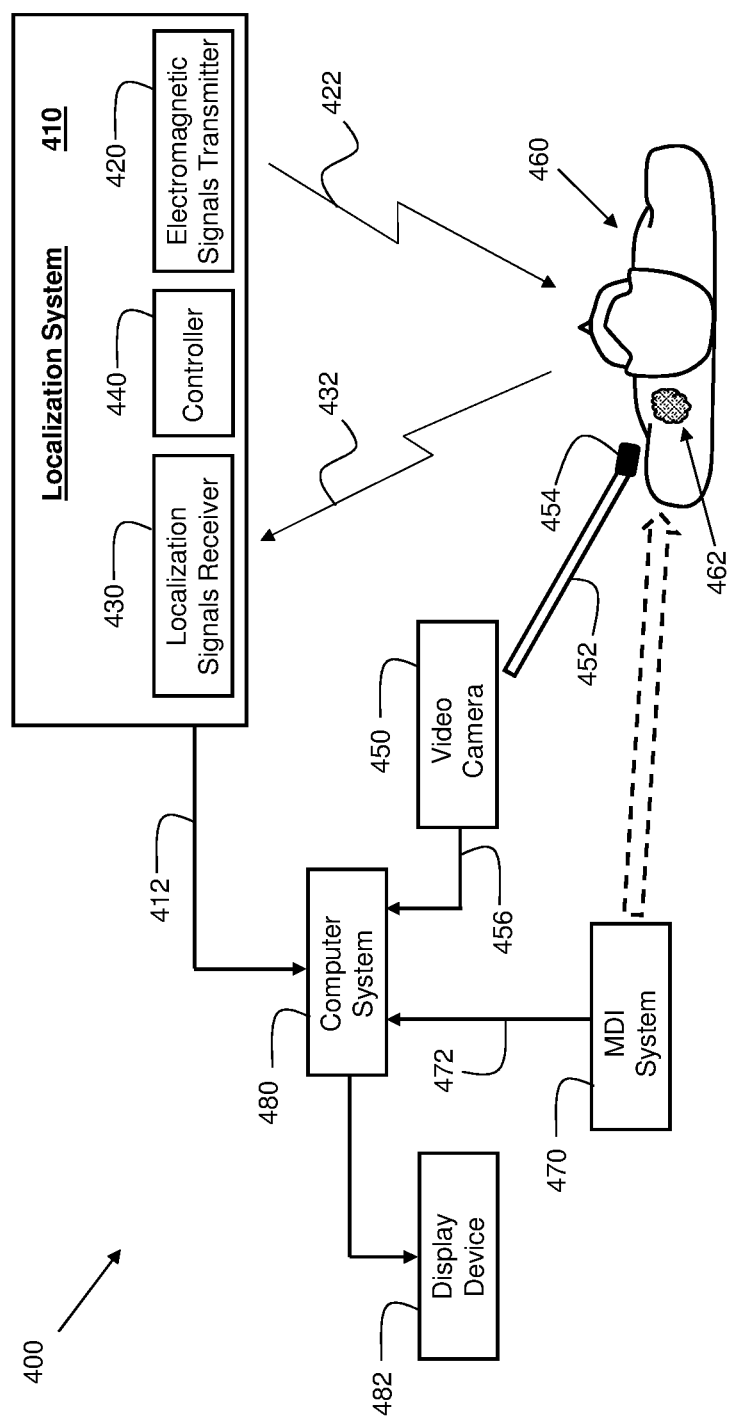
FIG. 4 is a schematic diagram illustrating a system for guiding a surgeon through surgery according to an example aspect.

FIG. 4 shows a block diagram of a system 400 for overlaying an SOI over images according to an example aspect. System 400 may include a localization system 410 to determine a location of sensorized passageways in a passageway system of an organ 462 in a patient 460, where one or more localization sensors are distributed in each sensorized passageway along the length of the sensorized passageway. System 400 may also include a video camera 450 for generating a stream of images 456 of organ 462. Video camera 450 may include one or more localization sensors 454 to localize video camera 450 by localization system 410 relative to the passageway system. System 400 may also include a controller 440 to control localization system 410 and a computer system 480 to control system 400. Computer system 480 may take on control tasks of controller 440 and thus function also as controller 440 or vice versa; controller 440 may take on control tasks of computer system 480 and thus also functions as computer system 480.

In some aspects, controller 440 may be configured to determine, based on a preoperative image including organ 462, a passageway system in organ 462, and an SOI of the organ 462, a location of the SOI in the preoperative image relative to the passageway system in the preoperative image; determine a location of the SOI relative to the reconstructed passageways based on the location of the SOI relative to the passageway system in the preoperative image; take an image of the organ by the video camera; co-align the passageway system with the taken image; determine a location of the SOI relative to the taken image based on the location of the SOI relative to the passageway system and the alignment between the passageway system and the taken image; and overlay on the taken image, an image object representing the SOI at the determined location of the SOI relative to the taken image.

Controller 440 may control operation of electromagnetic signals transmitter 420. For example, controller 440 may time the transmission of electromagnetic signals 422. Controller 440 may also control operation of electromagnetic localization signals receiver 430, for example controller 440 may time reception of electromagnetic signals 432 to the transmission of electromagnetic signals 422.

Controller 440 may determine the location of the SOI relative to the passageway system by synthesizing passageways in the passageway system, and by determining a spatial relationship between the resulting synthesized or reconstructed passageways and the passageway system in the preoperative image.

Synthesizing the organ passageways may include exchanging localization signals (e.g., 422, 432) between localization system 410 and multiple localization sensors that are distributed along the length of passageways to be synthesized. The passageways are in organ 462. The location of the diseased organ portion (DOP) relative to the passageway system may include mapping the relative location of the DOP in the preoperative image to the reconstructed passageway system. By way of example, the location of the DOP relative to the passageways in the preoperative image, which is shown at the location of DLP 305 in FIG. 3A, is mapped to the location of reconstructed DLP 305' shown in FIG. 3C. Aligning the image and the organ passageway system may include exchanging localization signals between localization system 410 and at least one localization sensor 454, which may be positioned in or in relation with video camera 450. Organ 462 may be, for example, a lung lobe, and the organ passageways may be, for example, lung airways.

Localization system 410 may be an electromagnetic localization system. Localization system 410 may include an electromagnetic signals transmitter 420 to transmit electromagnetic signals 422. Electromagnetic signals 422 may be configured such that they can be used to localize a device including a localization sensor. A localization sensor may be or include a conductive coil or a set of conductive coils (e.g., three, mutually-orthogonal coils), and it outputs a signal (e.g., a localization signal) as a function of the intensity of an electromagnetic field it senses in a certain direction, and, in addition, as a function of the spatial angle (e.g., orientation) between the conductive coil plane and the direction of the electromagnetic field. Localization system 410 may also include an electromagnetic localization signals receiver 430 to receive electromagnetic signals 432 from one or more localization sensors.

System 400 may also include a video camera 450, which may include a camera and a light source. Video camera 450 may also include a rod or tube 452 (e.g., which may form a portion of an endoscope) through which video camera 450 may take images of a patient 460, for example, images of a patient's lung that is suspected or has been diagnosed as having an SOI, for example, DOP. The image sensor of video camera 450 may be positioned at the distal end of tube 452 or at or near the proximal end of tube 452. A localization sensor 454 may be positioned at the distal end of tube 452 to enable determining the 2D or 3D location of the video camera 450 and hence the 2D or 3D location of images taken by video camera 450 relative to airways in the patient's lung. In other words, localization sensor 454 enables registration of images, which are taken by video camera 450, to lung airways of patient 460 and, through the patient's lung airways, to the SOI.

Electromagnetic signals 422 are intended to be sensed by localization sensors that are inserted through natural orifices of patient 460 and into airways of the patient's lungs. The localization sensors (not shown in FIG. 4) are inserted into some of a lung's airways and may stay there (e.g., by attaching them to the airways) while a surgery of the lung is in progress. The localization sensors may be inserted into the lung's airways by using one or more catheters. One or more localization sensors may be disposed on or in a catheter. The localization sensors may be configured to sense electromagnetic signals 422, and to concurrently transfer (432), to localization signals receiver 430, one or more corresponding output signals as a function of the position (location and/or orientation) of the localization sensors relative to electromagnetic signals transmitter 420. The localization sensors in the patient's airways may transfer the one or more output signals to localization signals receiver 430 wirelessly or via a communication cable.

System 400 may also include a medical diagnostic imaging (MDI) system 470 to preoperatively and non-invasively take images of internal tissues, organs etc., of patient 460. Computer system 480 may be functionally coupled to (1) localization system 410 to receive therefrom (412) localization data, (2) video camera 450 to receive therefrom (456) live images while surgery is in progress, and (3) MDI system 470 to receive therefrom (472) an image from which computer system 480 may determine the position/location and/or orientation, and optionally the shape and size, of SOI relative to airways in the patient's lung. Computer system 480 may be configured to execute any of the methods disclosed herein. For example, computer system 480 may be configured to execute the methods described in connection with FIGS. 2A-2C and 3A-3E. Computer system 480 may also function as controller 440. For example, computer system 480 may control the operation of localization system 410, and thus replace controller 440. Computer system 480 may include or be connected to a display device 482 to display images of the patient's lung with an object representing SOI 462 overlaid on the images at the correct position, namely, at a location corresponding to the position of the DLP relative to the airways as illustrated, for example, in FIGS. 3D and 3E.

The video camera's 450 location may be continually or continuously monitored in real-time throughout the surgical procedure. The video camera's location may be determined relative to the reconstructed airways. If the same localization system is used to: (1) localize the localization sensors used to reconstruct or synthesize the airways and (2) localize the localization sensors used to localize the video camera, determination of the position of the video camera relative to the reconstructed airways may be straightforward. However, if different localization systems are used, some coordinate transformations may be needed in order to determine the position of the video camera relative to the reconstructed airways.

In an aspect of the disclosure, display device 482 may simultaneously display two, spatially-aligned images in two display areas (DAs) (e.g., two juxtaposed DAs) on display device 482. One display area DA1 may display the MDI image (e.g., as a reference image) that includes a body organ that is undergoing the registration and surgical procedures described herein. Another display area DA2 may display real-time images of the surgery site. Real-time images of the surgery site include images that are continually taken by the video camera (e.g., by video camera 450) and displayed on display area DA2 while, and as long as, the surgical procedure is in progress.

The imaging perspective (e.g., angles and distance) from which the MDI image and the video camera images are captured may be different. For example, the surgeon may move the video camera laterally with respect to the surgical site, towards the organ (e.g., when zooming in) or away from organ (e.g., when zooming out), thus changing the field of view (FOV) and/or angle of imaging. In contrast, the MDI image is usually a preoperative snapshot image taken once at some particular FOV, imaging angle, and distance from the patient's body. In one aspect, every time the video camera operator (e.g., a surgeon) moves the video camera, for example, to change its imaging angle and/or FOV with respect to the organ (e.g., lung) being operated on, computer system 480 manipulates the MDI image to maintain spatial alignment and proportionality between the video camera images and the MDI image during the surgical procedure. For example, the computer system 480 rotates, translates, aligns, resizes, and/or downscales/upscales the image content, features, and/or objects in the MDI image in order for MDI image's content, features, and/or objects to follow or track corresponding changes in the image content of the video camera images (e.g., changes in the size, location, angles, and/or orientation of the SOI relative to the organ being operated on).

Manipulating an MDI image in the ways described herein is beneficial, for example, because it renders overlaying a reconstructed airway system of the body organ on the video camera images (as illustrated, for example, by FIG. 3D) unnecessary because the MDI image already shows the airway system. Another benefit of MDI image manipulation is that the MDI image includes additional image information that enables the surgical staff to see not only the airway system, but also other, various types of tissues that surround the SOI.

Figure 5:
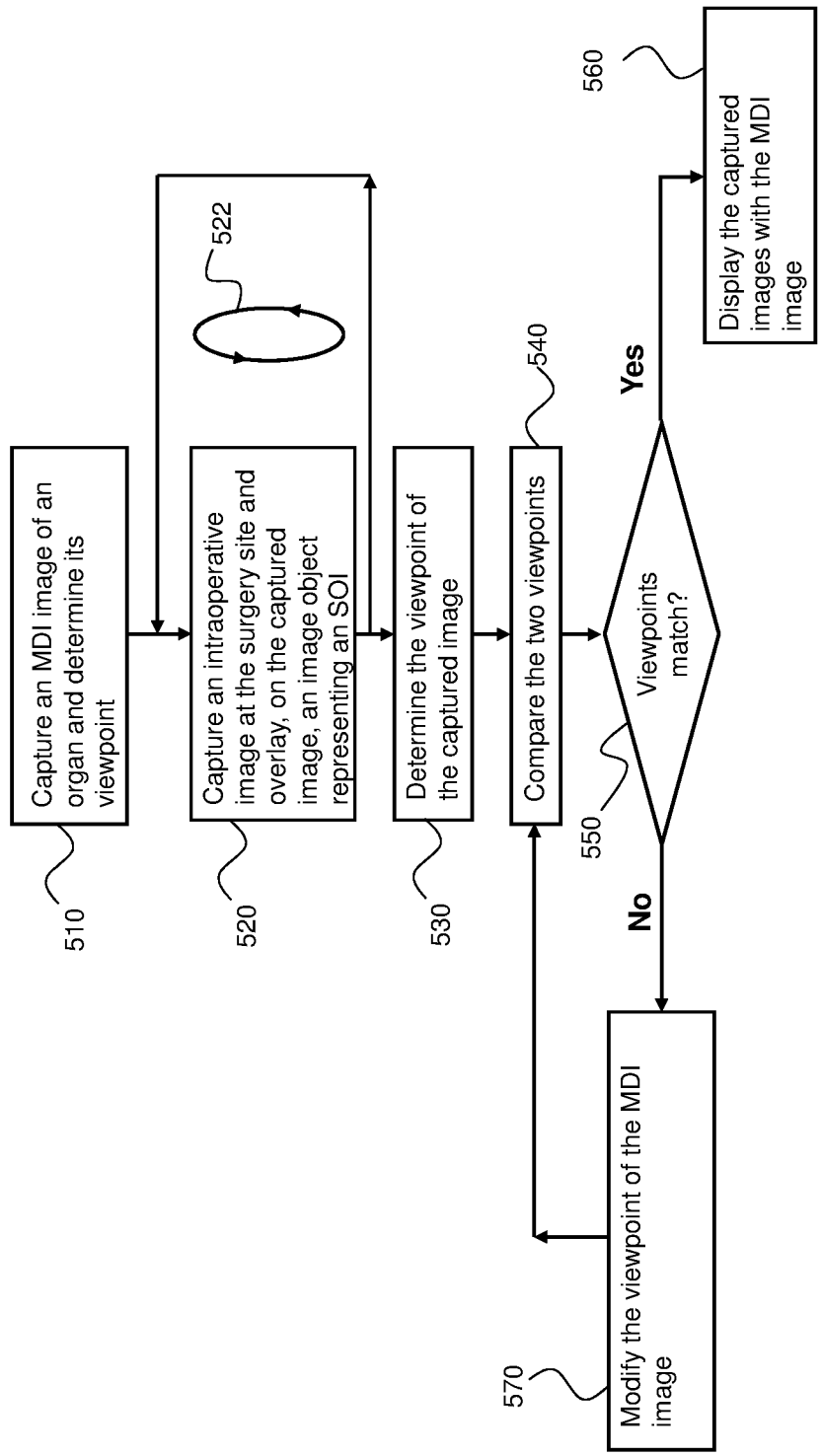
FIG. 5 is a flow diagram illustrating an intraoperative guiding method according to an example aspect.

FIG. 5 shows a guidance method according to an example aspect. FIG. 5 is described below in association with FIG. 4. At step 510, an MDI image (e.g., a CT image) containing an organ (e.g., a lung), a passageway system of the organ, and an SOI in or on the organ is captured by MDI system 470. Computer system 480 analyzes the MDI image to determine a viewpoint from which the MDI image was captured. Computer system 480 may determine the viewpoint based on, for example, voxel information that makes up the MDI image.

At step 520, an intraoperative image (e.g., a video image of an outside surface of an organ containing passageways) is captured or taken by video camera 450 at a surgery site. At step 520, computer system 480 optionally overlays, on the video camera image, an image object that represents the one or more SOIs. In some aspects, the image of the outside surface of the organ taken by the video camera is the same organ as shown in the MDI image. Video camera 450 continues (522) to capture or take images while the surgical procedure is in progress and steps 530-570 described below are repeated for all or a portion of newly captured images. In some aspects, an image object representing the SOI may not be overlaid on the video camera images if the MDI image, or a modified version of the MDI image, is overlaid on the video camera images because the MDI image may provide sufficient information to the surgical staff.

At step 530, computer system 480 determines the viewpoint of the captured image, for example, based on localization information obtained from localization sensors distributed in the organ's passageways, and from localization sensors mounted in or on the video camera 450. At step 540, computer system 480 compares the viewpoint of the MDI and the viewpoint of the captured image. If the two viewpoints match or are similar (this condition is shown as "Yes" at step 550), computer system 480 displays, at step 560, the captured image or images with the MDI image. However, if the two viewpoints do not match (this condition is shown as "No" at step 550), computer system 480 modifies the viewpoint of the MDI image at step 570, compares the two viewpoints at step 540, and if, at step 550, the viewpoints match or are similar, the computer system 480 displays the captured image or images with the modified MDI image at step 560.

Figure 6:
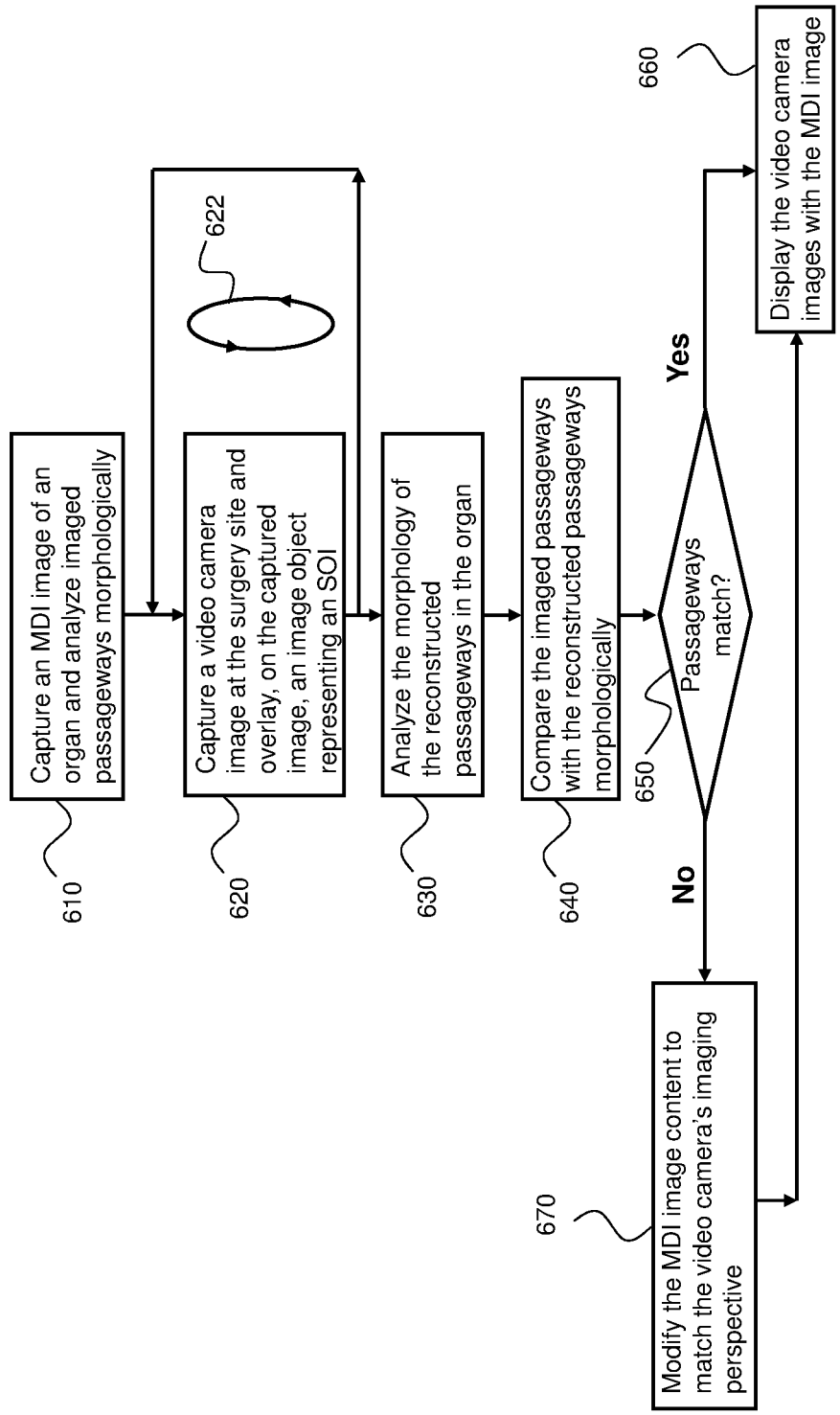
FIG. 6 is a flow diagram illustrating an intraoperative guiding method according to another example aspect.

FIG. 6 shows a guidance method according to another example aspect. FIG. 6 is described in association with FIG. 4. At step 610, an MDI image (e.g., a CT image of a lung) is captured by MDI system 470, and computer system 480 analyzes the MDI image morphologically, for example to detect or identify, in the MDI image, airways of the airway system of the lung. The result of the morphometrics analysis made by computer system 480 is morphological data that is related to the image content (e.g., passageways, one or more SOIs, anatomic structures, etc.) of the MDI image.

A CT image, which is an example of an MDI image, includes multiple image slices of an organ, where each image slice provides two-dimensional image information while adjacent image slices provide image information in a third (e.g., perpendicular) direction or dimension. The spatial position and/or orientation of an anatomic structure (e.g., of passageways, one or more SOIs, etc.), and the way some image features (e.g., some passageways) spatially relates to other image features (e.g., other passageways), may be determined, for example, by using voxels. A voxel represents a value on a grid in three-dimensional space. The position or coordinates of voxels are not explicitly encoded along with their values. Instead, the position of a voxel is determined based on its position relative to other, e.g., neighboring, voxels. The relative position of a voxel is determined in the image data structure that makes up a single volumetric image. A voxel is, therefore, a basic information unit that provides image information in three dimensions.

Therefore, a CT image inherently includes a coordinate system. The CT's inherent coordinate system enables a computer system not only to analyze a CT's image information and to compare image information to other image information, but also to manipulate voxels, for example, to modify (e.g., translate, rotate, resize, rescale, etc.) image objects (e.g., anatomical structures, SOIs, other tissues, etc.), or image content in general, according to needs, for example, according to display needs, for example to virtually change the imaging perspective. In the context of the disclosure, if needed, voxels may be manipulated and the related CT image modified so as to equate, adjust, match, or fit the CT image's or another MDI system's viewpoint to the imaging viewpoint of the video camera.

At step 620, a video camera image (e.g., a video camera image of an outside surface of an organ) is captured or taken by video camera 450 at a surgery site, and, optionally, computer system 480 overlays, on the captured image, an image object that represents the one or more SOIs. In some aspects, the image of the outside surface of the organ captured by the video camera is the same organ as shown in the MDI image. The way computer system 480 determines where to position the image object representing the one or more SOIs on the captured image and the way the image object should look is described herein. Video camera 450 continues (622) to capture or take images while the surgical procedure is in progress. An image object representing the SOI may not be overlaid on the one or more captured images if the MDI image, a modified MDI image, or a different preoperative image, is overlaid on the one or more preoperative images, for example, in the way described herein, for example in connection with FIGS. 5 and 6.

At step 630, computer system 480 morphologically analyzes the reconstructed passageways in the organ, and, at step 640, computer system 480 may morphologically compare the passageways as imaged by the MDI system (e.g., as imaged by a CT system) to the reconstructed passageways. The higher the morphological resemblance between passageways in the MDI image and the reconstructed passageways, the more the viewpoint (or virtual viewpoint) of the passageways in the MDI image resembles the viewpoint of the video camera taking the images of the organ containing the reconstructed passageways. If the morphological resemblance between the imaged passageways and the reconstructed passageways is low, or nonexistent, this means that digital data representing the image content of the MDI image needs to be manipulated in a way that would match the perspective (e.g., the virtual viewpoint or the pseudo-viewpoint) of the MDI image to the perspective from which the video camera captures or takes images of the organ containing the reconstructed passageways.

Localization information related to the location of the video camera may be compared to localization information that is obtained from the localization sensors that are distributed in the passageways, in order to determine the spatial imaging perspective, or imaging viewpoint, of the video camera.

At step 650, computer system 480 checks morphological differences between the reconstructed passageways and corresponding passageways in the MDI image in order to determine whether the two, related viewpoints match. If computer system 480 determines, at step 650, that there are no morphological differences between the reconstructed passageways and corresponding passageways in the MDI image, meaning that the two viewpoints match (that is, that the imaging perspective of the passageways in the MDI image resembles that of the reconstructed passageways; this condition is shown as "Yes" at step 650), computer system 480 displays, at step 660, the MDI image as is (without modifying it) in conjunction with the one or more images. The MDI image may be overlaid on the image in a way that the corresponding passageways of the MDI image would coincide with the reconstructed passageways. The MDI image may, alternatively, be displayed in conjunction or in association with the one or more images captured by the video camera 450.

However, if computer system 480 determines, at step 650, that the imaged passageways do not morphologically resemble the reconstructed passageways (this condition is shown as "No" at step 650), computer system 480 modifies, at step 670, the image content of the MDI image (e.g., by manipulating image voxels) in order for the corresponding passageways in the MDI image to resemble, match, or fit to the reconstructed passageways. As described herein, if the two types of passageways resemble one another, the viewpoint of the MDI image, after the modification (that is, the resulting pseudo viewpoint of the MDI image), matches, is in harmony with, or corresponds to the actual imaging perspective of the video camera. An MDI image is modified in a way that modifies the viewpoint of the MDI image. Since an MDI image is captured once from a real viewpoint, which is the viewpoint of the MDI system, a modified viewpoint of the MDI image is a virtual viewpoint or a pseudo viewpoint. In an alternative aspect, the MDI image content is modified in step 670 and steps 640 and 650 are repeated. Steps 640, 650, and 670 may be repeated until the modified MDI image of the passageways matches or substantially matches the reconstructed passageways morphologically.

The entire image content of an MDI image may be modified together; that is, each image element (e.g., each anatomical structure) in the MDI image may be modified image-wise in the same way (e.g., rotated in a same direction and/or by a same angle) such that all anatomical structures in the MDI image may be respectively displayed in a realistic way; that is, in a way that is congruent with, or matches, the video camera's viewpoint and hence congruent with real anatomical structures of the organ even though some or all of the real anatomical elements may be seen only partially in some or all of the images. In other words, the image content of the MDI image, or of any preoperative image, may be modified in a way that would make the various anatomical structures in the MDI image appear as if they were captured from the viewpoint of the video camera 450. This way, the medical staff performing the medical procedure may have a real sense of the whereabouts or position of the surgical instruments relative to the various anatomical structures of the organ being operated on and may perform the surgical procedure with improved accuracy.

After computer system 480 modifies, at step 670, the MDI image's viewpoint to match that of the reconstructed passageways, computer system 480 displays, at step 660, the images captured by the video camera 450 with the MDI image after having modified the viewpoint of the MDI image. In another aspect, steps 640 and 650 may be repeated after step 670 until the passageways match at step 650.

Method steps may be applied, for example, to every image that video camera 450 takes, or to every nth image (e.g., every 5th image, every 20th image, etc.) that video camera 450 takes, etc.

Computer system 480 calculates imaging parameters of or related to the MDI image and uses this calculation to adjust the image content of the MDI image (for example, to rotate it, resize it, and/or translate it) so that whenever the imaging perspective of the video camera changes (e.g., when the surgeon moves or repositions the video camera 450), the spatial orientation and other displaying parameters of the MDI image content would change in a corresponding manner in order for the MDI image content to be displayed (for example, in conjunction with the images captured by the video camera 450) as if the two images (the video camera image and the MDI image) were captured from the same imaging viewpoint (e.g., as if they were captured from the same or similar distance and/or from the same or similar imaging angle). The imaging perspective of the video camera, as used herein, may be measured or calculated with respect to the anatomic organ or passageway system of the organ. Spatially aligning an MDI image and a video camera image may include, among other things, spatially aligning passageways appearing in the MDI image and reconstructed passageways, for example, by computer system 480.

The aspects described herein refer to passageways which are at least partially located in the organ (i.e., the organ in which the SOI is located). However, any passageway system or passageways, which are dynamically associated with the organ, may be used or utilized according to the disclosure. A passageway system or passageways, which are dynamically associated with an organ, may include passageways which at least substantially move together with the organ or in a substantially identical manner (e.g., when the passageways are in the organ) or passageways in which their movement with respect to the organ and/or vice versa may be determined (e.g., modeled, measured or calculated). The term "movement" may include intrinsic movement, such as breathing, and/or extrinsic movement, such as a movement caused by a surgical tool or device.

The articles "a" and "an" are used herein to refer to one or more than one (i.e., at least one) of the grammatical object of the article, depending on the context. By way of example, depending on the context, "an element" can mean one element or more than one element. The term "including" is used herein to mean, and is used interchangeably with the phrase, "including but not limited to". The terms "or" and "and" are used herein to mean, and are used interchangeably with the term, "and/or," unless the context clearly indicates otherwise. The term "such as" is used herein to mean, and is used interchangeably with the phrase, "such as but not limited to".

Aspects may include a computer, processor, controller, and/or non-transitory storage medium, such as, for example, a memory, a disk drive, or a USB flash memory, encoding, including, or storing instructions, e.g., computer-executable instructions, which, when executed by a computer, processor, or controller, carry out methods disclosed herein.

Having thus described example aspects of the disclosure, it will be apparent to those skilled in the art that modifications of the disclosed aspects will be within the scope of the disclosure. Alternative aspects may, accordingly, include more modules, fewer modules and/or functionally equivalent modules.

The disclosure is relevant to various types of MDI systems (e.g., CT, MRI, and the like), to various video cameras, and to various types of localization systems, devices, or sensors. Therefore, the scope of the claims that follow is not limited to any particular MDI system, video camera, localization system, device, or sensor. The disclosure is also relevant to various types of body organs and preoperative images other than MDI images, and applicable to multiple SOIs, DOPs, and DLPs that may be located at the same body site or in different body sites and operated on during a same surgical procedure.

The term "overlay" and its various derivatives, as referred to herein, may include superimposing information, e.g., by adding or combining information, such as image information (also referred to herein as "image"). For example, an image may be superimposed on a view (e.g., another image) to provide a composite view. The term "overlay" and its various derivatives, as referred to herein, may also include the replacing of information, e.g., by removing a piece of information (e.g., a portion of an image) and placing another piece of information in its stead (e.g., a portion of another image) or by covering the piece of information with the another piece of information.

The term "structure of interest" (SOI), as referred to herein, may include an element, biological or artificial, such as an anatomical region of interest in a patient's body (i.e., an anatomical SOI). For example, an SOI may be or may include a tissue (including soft tissue and bone tissue), an organ, an implant or a fiducial marker. An anatomical SOI may be, or may include, for example, a diseased tissue or organ portion, or a healthy tissue or organ portion, or both diseased and healthy tissues or organ portions.

The term "morphology", as used herein, means "mathematical morphology", which is a theory and technique used in the analysis and processing of geometrical structures. Mathematical morphology is most commonly applied to digital images. Morphology, as used herein, may depend on the viewing angle, meaning that an image object may have different morphologies if viewed from different angles. Morphometrics, as used herein, refers to the quantitative analysis of form, including size, shape, geometry, angles, and proportionality between image elements, for example, of and between individual passageways contained in an MDI image and in a video image. Morphometrics analysis may be performed by using various image processing techniques in order to identify, for example, anatomical structures in the analyzed image, for the purpose of, for example, comparing spatial relationships between anatomical structures that are contained in the images that are subject of the comparison.

Although aspects are not limited in this regard, discussions utilizing terms such as, for example, "processing," "computing," "calculating," "determining", "estimating", "evaluating", "analyzing", "checking", or the like, may refer to one or more operations and/or processes of a computer, a computing system or other electronic computing device (e.g., controller), that manipulate and/or transform data represented as physical (e.g., electronic) quantities within the computer's registers and/or memories into other data similarly represented as physical quantities within the computer's registers and/or memories or other non-transitory storage medium that may store instructions to perform operations and/or processes. Unless explicitly stated, the example methods described herein are not limited to a particular order or sequence. Additionally, some of the described methods or steps thereof can, for example, occur or be performed at the same point in time.

Medical diagnostic imaging (MDI) refers to a variety of non-invasive methods for detecting, identifying, and monitoring, for example, diseases or injuries through the generation of images of various internal anatomical structures, organs, and a pathology (e.g., tumor) in the patient's body. The detailed images produced by these procedures are used to inform the patient and physician about the anatomic organization and functional working of the inner organs and structure of the patient's body, and also for treating of and operating on, for example, diseased body organs. Radiologists and other physicians interpret the resulting MDI images to diagnose, e.g., medical illness or injury so that specific patient treatment and therapy can be planned and implemented. Diagnostic imaging is also used to guide surgical planning and is often used to follow surgery and/or monitor the result of therapeutic procedures. Diagnostic imaging techniques include, for example, ultrasound (US), magnetic resonance (MR) and computed tomography (CT), as well as traditional x-ray or radiology.

Video-assisted thoracoscopic surgery (VATS) is a type of thoracic surgery performed using a small video camera that is introduced into the patient's chest via small incisions. The instrumentation for VATS includes a camera-linked fiber-optic scope and conventional thoracic instruments or laparoscopic instruments. Using the VATS's camera, the surgeon can view the instruments that are used along with the anatomy on which the surgeon is operating. The camera's fiber-optics and instruments are inserted through separate holes (or ports) in the chest wall. The camera (e.g., a charge coupled device (CCD) type camera), which provides "regular" (e.g., R-G-B) images (i.e., video images) of the body organ that is treated, may be maintained at some distance away from, and external to, the treated body organ in order to visualize the entire treated body organ and the vicinity thereof. If the surgeon's attention is focused on a particular area or spot, the surgeon can operate the camera to zoom in on the particular area or spot, or the surgeon can move the camera closer to the particular area or spot. VATS has many applications, one of which is in pulmonary surgery. As described herein, the VATS's video camera can take images of the surface of the organ to be operated on, but it cannot take images of the internal parts or anatomical structures of the organ unless the surgeon cuts a way through the organ to make the internal parts of the organ visible to the video camera. In the case of pulmonary surgery, the VATS's video camera cannot see the diseased lung portion inside the lung that is to be operated on, so, with the absence of line of site to the lung's internal anatomical structures, the surgeon may cut the lung in the wrong place and/or unintentionally cut a healthy or sensitive tissue or organ.

Some of the example methods and systems shown in the drawings and described herein are described in the context of surgery that is performed on the lungs while utilizing a video camera. However, the same or similar methods and systems, including imaging devices other than a video camera, may be used to guide surgeons when operating on other organ systems that include a system of anatomical passageways/lumens.

There could be multiple SOIs that the surgeon may want to operate on (e.g., to remove or resect them) during the same surgical procedure, and the systems and methods described herein are applicable to these cases as well. For example, lobectomy procedures involve resection of the pulmonary arteries, the pulmonary veins, and the bronchi leading to the lobe, so each pulmonary element may be regarded as an anatomical SOI. An anatomical SOI may include one or more organ objects that may be in or related to a same organ that is operated on, or to multiple organs that are operated on during a same surgical procedure. An anatomical SOI may be or include an anatomic structure such as a diseased organ portion, a diseased lung portion, abnormal tissue, an abnormal organ, or a benign anatomic structure.

Anything (e.g., any operation, method step, benefit, etc.) that is described herein as applicable, attributed, or related to an MDI image is likewise applicable, attributed, or related to any type of preoperative image.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A system comprising:
an endoscope;
a display;
a processor operatively coupled to the endoscope and the display; and
a memory having stored thereon a preoperative image of a body structure and a structure of interest (SOI), and instructions, which, when executed by the processor, cause the processor to:
determine a location of the SOI relative to the body structure in the preoperative image;
generate a reconstructed body structure;
determine a location of the SOI relative to the reconstructed body structure based on the preoperative image;
receive an intraoperative image captured by the endoscope and a corresponding location of the endoscope;
align the location of the endoscope with the reconstructed body structure, yielding an aligned location of the endoscope;
determine a location of the SOI relative to the intraoperative image based on the location of the SOI relative to the reconstructed body structure and the aligned location of the endoscope; and display, on the display, the intraoperative image and an object representing the SOI overlaid on the intraoperative image at the location of the SOI relative to the intraoperative image.

2. The system of claim 1, wherein the body structure includes passageways, and
wherein the instructions further cause the processor to:
reconstruct the passageways, yielding reconstructed passageways;
determine a spatial relationship between the reconstructed passageways and the passageways in the preoperative image; and
map the location of the SOI relative to the passageways in the preoperative image to the location of the reconstructed passageways.

3. The system of claim 2, further comprising at least one location sensor,
wherein the body structure includes passageways, and
wherein the instructions further cause the processor to:
receive location data from at least one location sensor in the passageways; and
reconstruct the passageways based on the location data.

4. The system of claim 1, further comprising at least one location sensor coupled to the endoscope,
wherein the instructions further cause the processor to determine, at a time the intraoperative image is captured, the location of the endoscope relative to the location of the reconstructed body structure based on location information from the at least one location sensor.

5. The system of claim 1, wherein the body structure includes airways of a lung.

6. The system of claim 1, wherein the instructions further cause the processor to:
generate the object representing the SOI; and
apply morphological properties of the SOI in the preoperative image to the object.

7. The system of claim 1, wherein the instructions further cause the processor to modify the preoperative image according to a change in an imaging perspective of the endoscope with respect to the body structure.

8. The system of claim 7, wherein the change in the imaging perspective of the endoscope includes a change in distance between the endoscope and the body structure or a change in an imaging angle of the endoscope.

9. The system of claim 7, wherein the instructions further cause the processor to modify a size, a shape, a proportionality, or an orientation of a feature of the preoperative image.

10. The system of claim 7, wherein the instructions further cause the processor to display the modified preoperative image together with the intraoperative image.

11. The system of claim 1, wherein the instructions further cause the processor to modify the preoperative image such that a viewpoint of the preoperative image matches a viewpoint of the intraoperative image.

12. The system of claim 1, wherein the SOI includes an anatomic structure selected from the group consisting of a diseased organ portion, a diseased lung portion, an abnormal tissue, an abnormal organ, a benign anatomic structure, and an organ structure.

13. A system comprising:
a display;
a processor operatively coupled to the display; and
a memory having stored thereon at least one radiographic image of passageways associated with a body structure and a structure of interest (SOI), and instructions, which, when executed by the processor, cause the processor to:
determine a location of the SOI relative to the passageways based on the at least one radiographic image of the passageways;
receive endoscopic images;
determine a location of the SOI relative to each endoscopic image based on the location of the SOI relative to reconstructed passageways and a relationship between each endoscopic image and the reconstructed passageways;
overlay an object representing the SOI on each endoscopic image at the location of the SOI relative to each endoscopic image, yielding modified endoscopic images; and
display, by the display, the modified endoscopic images.

14. The system of claim 13, wherein the instructions further cause the processor to:
generate the object representing the SOI; and
applying a size, a shape, and an orientation to the object complying with a size, a shape, and an orientation of the SOI relative to the passageways in the at least one radiographic image of the passageways.

15. The system of claim 13, wherein the instructions further cause the processor to:
modify the at least one radiographic image such that a viewpoint of the radiographic image matches a viewpoint of the endoscopic images, yielding at least one modified image; and
displaying, by the display, the at least one modified image together with the endoscopic images.

16. A system comprising:
at least one location sensor;
an endoscope configured to capture intraoperative images within body passageways; and
a processor; and
a memory having stored thereon a preoperative image of body passageways and a structure of interest (SOI), and instructions, which, when executed by the processor, cause the processor to:
receive location information from the at least one location sensor in the body passageways;
reconstruct the body passageways based on the location information, yielding reconstructed body passageways;
determine, based on the preoperative image, a location of the SOI relative to the body passageways in the preoperative image;
determine, based on the location of the SOI relative to the body passageways in the preoperative image, a location of the SOI relative to the reconstructed body passageways;
receive, from the endoscope, an intraoperative image;
determine a location of the endoscope relative to a location of the reconstructed body passageways;
determine a location of the SOI relative to the intraoperative image based on the location of the SOI relative to the reconstructed body passageways and the location of the endoscope relative to the location of the reconstructed body passageways; and
overlay an object representing the SOI on the intraoperative image at the location of the SOI relative to the intraoperative image.

17. The system of claim 16, wherein the instructions further cause the processor to:

determine the location of the SOI relative to the reconstructed body passageways by determining a spatial relationship between the reconstructed body passageways and the body passageways in the preoperative image; and determine the location of the SOI relative to the reconstructed body passageways by mapping the location of the SOI in the preoperative image to the reconstructed body passageways.

18. The system of claim 17, wherein the at least one location sensor is coupled to a catheter, and
wherein the instructions further cause the processor to:
receive location information from the at least one location sensor as the catheter passes through the body passageways; and
reconstruct the body passageways based on the location information.

19. The system of claim 16, wherein two or more location sensors are coupled to a catheter and the location information is received from the two or more location sensors.

20. The system of claim 16, wherein the instructions further cause the processor to:
modify the preoperative image according to a change in a distance of the endoscope from the SOI or according to a change in an angle at which the endoscope captures the intraoperative images, yielding a modified preoperative image; and
display the modified preoperative image on the display together with the intraoperative images.

* * * * *